(12) United States Patent
Wright et al.

(10) Patent No.: US 10,103,334 B2
(45) Date of Patent: Oct. 16, 2018

(54) COMPOSITIONS WITH TRIARYLAMINE DERIVATIVES AND OLED DEVICE CONTAINING THE SAME

(71) Applicant: Dow Global Technologies LLC, Midland, MI (US)

(72) Inventors: Robert Wright, Sugarland, TX (US); Kyoung moo Koh, Midland, MI (US); Liam Spencer, Manvel, TX (US); David Devore, Midland, MI (US); Dean Welsh, Midland, MI (US); Timothy De Vries, Midland, MI (US); Bruce Bell, Higgins Lake, MI (US); Matthias Ober, Midland, MI (US); Sukrit Mukhopadhyay, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 15/540,315

(22) PCT Filed: Dec. 28, 2015

(86) PCT No.: PCT/US2015/067591
§ 371 (c)(1),
(2) Date: Jun. 28, 2017

(87) PCT Pub. No.: WO2016/109386
PCT Pub. Date: Jul. 7, 2016

(65) Prior Publication Data
US 2018/0006225 A1    Jan. 4, 2018

Related U.S. Application Data

(60) Provisional application No. 62/097,310, filed on Dec. 29, 2014.

(51) Int. Cl.
*C07D 209/86* (2006.01)
*H01L 51/00* (2006.01)
*H01L 51/50* (2006.01)

(52) U.S. Cl.
CPC .......... *H01L 51/006* (2013.01); *C07D 209/86* (2013.01); *H01L 51/0052* (2013.01);
(Continued)

(58) Field of Classification Search
CPC .................................................. C07D 209/86
See application file for complete search history.

(56) References Cited

U.S. PATENT DOCUMENTS 8,106,391 B2    1/2012  Endo et al.
2010/0327270 A1   12/2010  Buesing et al.
(Continued)

FOREIGN PATENT DOCUMENTS

JP    2005294188 A    10/2005
KR    1468087 B1 *  12/2014    .......... C07D 405/12
(Continued)

OTHER PUBLICATIONS

Machine translation of KR 1468087 B1, obtained from KIPRIS on Oct. 11, 2017 (Year: 2017).*

*Primary Examiner* — Matthew P Coughlin

(74) *Attorney, Agent, or Firm* — Husch Blackwell LLP

(57) ABSTRACT

The present disclosure provides a composition. In an embodiment, a composition is provided and comprises a Compound 1 shown below: For Compound 1, $R_1$ through $R_{24}$ are the same or different. $R_1$ through $R_{24}$ each is independently selected from the group consisting of hydrogen, unsubstituted hydrocarbyl, substituted hydrocarbyl, cyano, alkoxy, aryloxy, and $NR'_2$. R' is hydrogen or hydrocarbyl; wherein two or more of adjacent $R_1$ to $R_{24}$ may optionally form one or more ring structures. The Component Z is selected from the group consisting Group Z-1, Group Z-2, Group Z-3, Group Z-4, Group Z-5, Group Z-6 and Group Z-7 shown below: For Compound 1, one or more hydrogen atoms may optionally be substituted with deuterium.

(Compound 1)

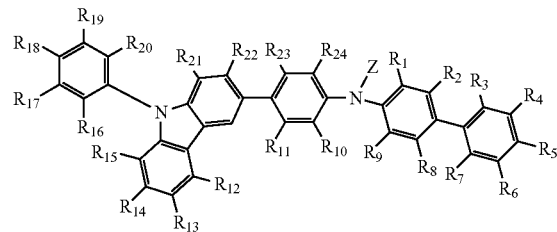

Group Z-1

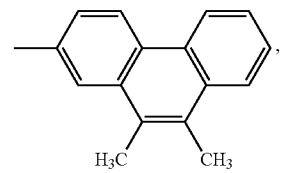

Group Z-2

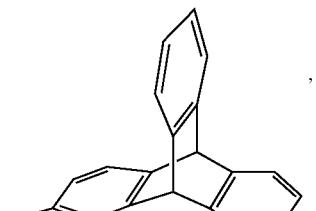

(Continued)

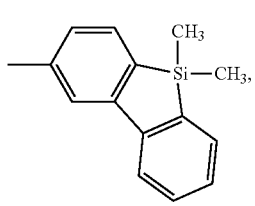

Group Z-3

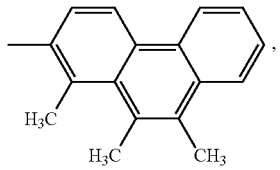

Group Z-4

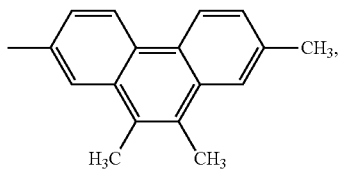

Group Z-5

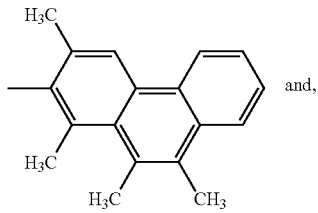

Group Z-6

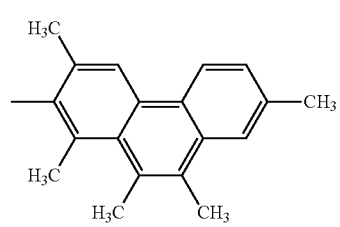

Group Z-7

18 Claims, No Drawings

(52) U.S. Cl.
CPC ...... *H01L 51/0055* (2013.01); *H01L 51/0061* (2013.01); *H01L 51/0072* (2013.01); *H01L 51/0094* (2013.01); *H01L 51/001* (2013.01); *H01L 51/5056* (2013.01); *H01L 2251/552* (2013.01)

(56) References Cited

U.S. PATENT DOCUMENTS

| | | |
|---|---|---|
| 2013/0228753 A1 | 9/2013 | Moon et al. |
| 2016/0211794 A1 | 7/2016 | Kim et al. |
| 2017/0170398 A1 | 6/2017 | Spencer et al. |
| 2017/0170400 A1 | 6/2017 | Spencer et al. |

FOREIGN PATENT DOCUMENTS

| | | | |
|---|---|---|---|
| WO | 2014/209050 A1 | 12/2014 | |
| WO | WO-2014209050 A1 * | 12/2014 | ........... C07D 405/12 |
| WO | 2016/026265 A1 | 2/2016 | |
| WO | WO-2016026123 A1 * | 2/2016 | ............. C08G 61/12 |
| WO | WO-2016026265 A1 * | 2/2016 | ......... H01L 51/0034 |
| WO | WO-2016026266 A1 * | 2/2016 | ......... H01L 51/0034 |
| WO | WO-2016026451 A1 * | 2/2016 | ............. C08G 61/12 |
| WO | WO-2016028906 A1 * | 2/2016 | ........... H01L 51/004 |

\* cited by examiner

COMPOSITIONS WITH TRIARYLAMINE DERIVATIVES AND OLED DEVICE CONTAINING THE SAME

REFERENCE TO RELATED APPLICATIONS

This application claims priority to U.S. provisional patent application No. 62/097,310 filed on 29 Dec. 2014, the entire content of which is incorporated by reference herein.

BACKGROUND

An OLED (organic light-emitting diode) is a light-emitting diode (LED), in which the emissive electroluminescent layer is a film of an organic compound, which emits light in response to an electric current. A typical OLED has a multi-layer structure, and typically includes an indium tin oxide (ITO) anode, and a metal cathode. Sandwiched between the ITO anode and the metal cathode are several organic layers, such as a hole injection layer (HIL), a hole transfer layer (HTL), an emitting material layer (EML), an electron transfer layer (ETL), and an electron injection layer (EIL).

Several properties required for such electroluminescent and charge transport compounds include high fluorescent quantum yield in solid state, high mobility of electrons and holes, chemical stability during vapor-deposition in vacuum, and the ability to form stable films. Common problems with OLEDs include fast aging/short life span, undesirably high operating voltages, or insufficient efficiency. The art recognizes the on-going need for new materials that enable longer device life span, lower operating voltages, and greater efficiency. The art recognizes the need for such light-emissive materials for the hole transport layer of OLEDs in particular.

SUMMARY

The present disclosure provides compositions directed to a novel class of triarylamine-based compounds, and derivatives thereof for OLED devices and OLED hole transport layer in particular.

The present disclosure provides a composition. In an embodiment, a composition is provided and comprises a Compound 1 shown below:

For Compound 1, $R_1$ through $R_{24}$ are the same or different and $R_1$ through $R_{24}$ each is independently selected from the group consisting of hydrogen, unsubstituted hydrocarbyl, substituted hydrocarbyl, cyano, alkoxy, aryloxy, and $NR'_2$. $R'$ is hydrogen or hydrocarbyl; wherein two or more of adjacent $R_1$ to $R_{24}$ may optionally form one or more ring structures. The Component Z is selected from the group consisting of Group Z-1, Group Z-2, Group Z-3, Group Z-4, Group Z-5, Group Z-6 and Group Z-7 shown below:

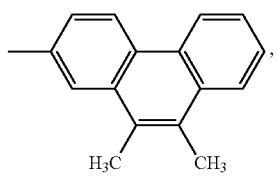

Group Z-1

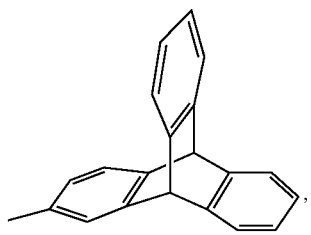

Group Z-2

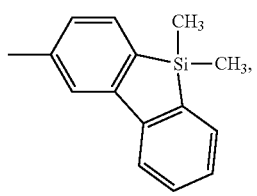

Group Z-3

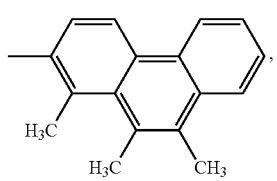

Group Z-4

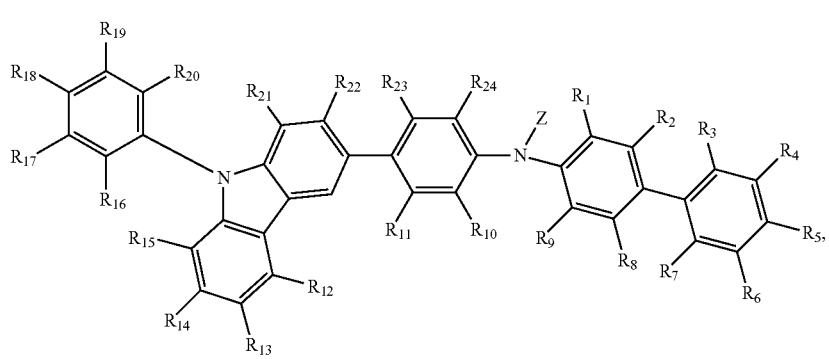

(Compound 1)

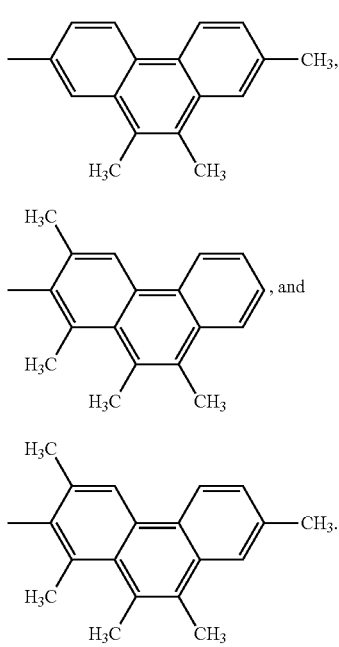

For Compound 1, one or more hydrogen atoms may optionally be substituted with deuterium.

The present disclosure provides a film. In an embodiment, a film is formed from the present composition. The composition can include Compound 1 or two or more Compound 1s, each Compound 1 having a different Z Component selected from Group Z-1 through Group Z-7.

The present disclosure provides an electronic device. In an embodiment, an electronic device is provided that contains a component (such as a film layer) formed from the present composition. The composition in the electronic device can include Compound 1 or two or more Compound 1s, each Compound 1 having a different Z Component selected from Group Z-1 through Group Z-7.

Definitions

Unless stated to the contrary, implicit from the context, or customary in the art, all parts and percents are based on weight. For purposes of United States patent practice, the contents of any referenced patent, patent application or publication are incorporated by reference in their entirety (or its equivalent US version is so incorporated by reference) especially with respect to the disclosure of definitions (to the extent not inconsistent with any definitions specifically provided in this disclosure) and general knowledge in the art.

The numerical ranges disclosed herein include all values from, and including, the lower value and the upper value. For ranges containing explicit values (e.g., 1 or 2, or 3 to 5, or 6, or 7) any subrange between any two explicit values is included (e.g., 1 to 2; 2 to 6; 5 to 7; 3 to 7; 5 to 6; etc.).

The term "alkoxy," as described herein, refers to an alkyl in which at least one hydrogen atom is substituted with an oxygen atom, 0.

The term "alkyl," as described herein, refers to an organic radical derived from an aliphatic hydrocarbon by deleting one hydrogen atom therefrom. An alkyl group may be a linear, branched, cyclic or a combination thereof. The term "substituted alkyl," as used herein, refers to an alkyl, in which at least one hydrogen atom is substituted with a substituent that comprises at least one heteroatom. Heteroatoms include, but are not limited to, O, N, P and S. Substituents include, but are not limited to, halide, OR', NR'$_2$, PR'$_2$, P(=O)R'$_2$, SiR'$_3$; where each R' is independently a $C_1$-$C_{20}$ hydrocarbyl group.

The "anode" injects holes into a layer located on the emitting layer side, such as the hole injection layer, the hole transport layer, or the emitting layer. The anode is disposed on the substrate. The anode is typically made from a metal, a metal oxide, a metal halide, an electroconductive polymer, and combinations thereof.

The term "aryl," as described herein, refers to an organic radical derived from aromatic hydrocarbon by deleting one hydrogen atom therefrom. An aryl group may be a monocyclic and/or fused ring system, each ring of which suitably contains from 5 to 7, preferably from 5 or 6 atoms. Structures wherein two or more aryl groups are combined through single bond(s) are also included. Specific examples include, but are not limited to, phenyl, tolyl, naphthyl, biphenyl, anthryl, indenyl, fluorenyl, benzofluorenyl, phenanthryl, triphenylenyl, pyrenyl, perylenyl, chrysenyl, naphtacenyl, fluoranthenyl and the like. The naphthyl may be 1-naphthyl or 2-naphthyl, the anthryl may be 1-anthryl, 2-anthryl or 9-anthryl, and the fluorenyl may be any one of 1-fluorenyl, 2-fluorenyl, 3-fluorenyl, 4-fluorenyl and 9-fluorenyl. The term "substituted aryl," as used herein, refers to an aryl, in which at least one hydrogen atom is substituted with a substituent comprising at least one heteroatom, and any combination thereof. Heteroatoms include, but are not limited to, O, N, P and S. Substituents include, but are not limited to, halide OR', NR'$_2$, PR'$_2$, P(=O)R'$_2$, SiR'$_3$; where each R' is independently a $C_1$-$C_{20}$ hydrocarbyl group.

The term "aryloxy," as described herein, refers to an aryl in which at least one hydrogen atom is replaced with an oxygen atom, 0.

The terms "comprising," "including," "having," and their derivatives, are not intended to exclude the presence of any additional component, step or procedure, whether or not the same is specifically disclosed. In order to avoid any doubt, all compositions claimed through use of the term "comprising" may include any additional additive, adjuvant or compound, whether polymeric or otherwise, unless stated to the contrary. In contrast, the term, "consisting essentially of" excludes from the scope of any succeeding recitation any other component, step or procedure, excepting those that are not essential to operability. The term "consisting of" excludes any component, step or procedure not specifically delineated or listed.

The "cathode" injects electrons into a layer located on the emitting layer side (i.e., the electron injection layer, electron transport layer, or the emitting layer). The cathode is typically made from a metal, a metal oxide, a metal halide, an electroconductive polymer, and combinations thereof.

The term "cyano," as described herein, refers to a radical with the molecular formula .CN. The cyano may be derived by removing the hydrogen atom from cyanic acid, HCN.

"Dopant" and like terms, refer to a material that undergoes radiative emission from an excited state. The excited state can be generated by application of electrical current in an electroluminescent device.

"Electron injection layer," or "EIL," and like terms is a layer for efficiently injecting electrons injected from the cathode into the electron transport layer.

"Electron transport layer," or "ETL," and like terms is a layer disposed between the emitting layer and the electron injection layer for improving the luminescent efficiency of the OLED. When placed in an electric field, the electron transport layer transports electrons injected from the cathode toward the emitting layer. The material or composition of the ETL typically has a high electron mobility for efficiently transporting injected electrons.

"Electron Volt" or "eV" is the amount of energy gained (or lost) by the charge of a single electron moved across an electric potential difference of one volt.

"Emitting layer" and like terms, is a layer located between electrodes (anode and cathode) and when placed in an electric field is excited by the recombination of holes injected from the anode through the hole injection layer with electrons injected from the cathode through the electron transport layer, the emitting layer being the primary light-emitting source. The emitting layer consists of host and dopant. The host material could be bipolar or unipolar, and may be used alone or by combination of two or more host materials. The opto-electrical properties of the host material may differ to which type of dopant (Phosphorescent or Fluorescent) is used. For Fluorescent dopants, the assisting host materials should have good spectral overlap between adsorption of the dopant and emission of the host to induce good Forster transfer to dopants. For phosphorescent dopants, the assisting host materials should have high triplet energies to confine triplets of the dopant.

The term "heteroalkyl," as described herein, refers to an alkyl group, in which at least one carbon atom or CH group or $CH_2$ is substituted with a heteroatom or a chemical group containing at least one heteroatom. Heteroatoms include, but are not limited to, O, N, P and S. A heteroalkyl group may be a linear, branched, cyclic or a combination thereof. The term "substituted heteroalkyl," as used herein, refers to an heteroalkyl, in which at least one hydrogen atom is substituted with a substituent that comprises at least one heteroatom. Heteroatoms include, but are not limited to, O, N, P and S. Substituents include, but are not limited to, halide, OR', $NR'_2$, $PR'_2$, $P(=O)R'_2$, $SiR'_3$; where each R' is independently a $C_1$-$C_{20}$ hydrocarbyl group.

The term "heteroaryl," as described herein, refers to an aryl group, in which at least one carbon atom or CH group or $CH_2$ is substituted with a heteroatom or a chemical group containing at least one heteroatom. Heteroatoms include, but are not limited to, O, N, P and S. The heteroaryl may be a 5- or 6-membered monocyclic heteroaryl or a polycyclic heteroaryl which is fused with one or more benzene ring(s), and may be partially saturated. The structures having one or more heteroaryl group(s) bonded through a single bond are also included. The heteroaryl groups may include divalent aryl groups of which the heteroatoms are oxidized or quarternized to form N-oxides, quaternary salts, or the like. Specific examples include, but are not limited to, monocyclic heteroaryl groups, such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl; polycyclic heteroaryl groups, such as benzofuranyl, fluoreno[4,3-b]benzofuranyl, benzothiophenyl, fluoreno[4,3-b]benzothiophenyl, isobenzofuranyl, benzimidazolyl, benzothiazolyl, benzisothiazolyl, benzisoxazolyl, benzoxazolyl, isoindolyl, indolyl, indazolyl, benzothia-diazolyl, quinolyl, isoquinolyl, cinnolinyl, quinazolinyl, quinoxalinyl, carbazolyl, phenanthridinyl and benzodioxolyl; and corresponding N-oxides (for example, pyridyl N-oxide, quinolyl N-oxide) and quaternary salts thereof. The term "substituted heteroaryl," as used herein, refers to a heteroaryl in which at least one hydrogen atom is substituted with a substituent composed of an unsubstituted alkyl, a substituted alkyl, at least one heteroatom, and any combination thereof. Heteroatoms include, but are not limited to, O, N, P and S. Substituents include, but are not limited to, halide OR', $NR'_2$, $PR'_2$, $P(=O)R'_2$, $SiR'_3$; where each R' is independently a $C_1$-$C_{20}$ hydrocarbyl group.

A "heteroatom" is an atom other than carbon or hydrogen. Nonlimiting examples of heteroatoms include: F, Cl, Br, N, O, P, B, S, Si, Sb, Al, Sn, As, Se and Ge.

"Hole injection layer," or "HIL," and like terms, is a layer which transports holes from the anode to the emitting layer. The hole injection layer is typically formed on the anode.

"Hole transport layer (or "HTL")," and like terms, refers to a layer made from a material, which transports holes. High hole mobility is recommended for OLED devices. The HTL is used to help block passage of electrons transported by the emitting layer. Small electron affinity is typically required to block electrons. The HTL should desirably have larger triplets to block exciton migrations from an adjacent EML layer.

The term "hydrocarbon," as used herein, refers to a chemical group containing only hydrogen atoms and carbon atoms. The term "hydrocarbon" includes "a hydrocarbyl"" which is a hydrocarbon substituent having a valence (typically univalent). The term "substituted hydrocarbon," (or "substituted hydrocarbyl"), as used herein, refers to a hydrocarbon (or hydrocarbyl) in which at least one hydrogen atom is substituted with a substituent comprising at least one heteroatom. Heteroatoms include, but are not limited to, a halide, O, N, P and S. Substituents include, but are not limited to, halide, OR', $NR'_2$, $PR'_2$, $P(=O)R'_2$, $SiR'_3$; where each R' is independently a $C_1$-$C_{20}$ hydrocarbyl group. An "unsubstituted hydrocarbon" (or "unsubstituted hydrocarbyl") is a hydrocarbon that contains no heteroatoms.

The term "independently," or "each is independently selected from," or like terms refers to the separate selection of an element for each individual member within a target group. For example, the term "for each of Compound 1 through Compound 5, independently, $R_1$ through $R_5$ each independently is selected from gold, silver, and copper" means (i) the property of a given substituent $R_1$-$R_5$ with respect to each Compound 1-5 is separate and individual (i.e., $R_1$ (gold) of Compound 1 can be the same or different element as $R_1$ (gold, silver, or copper) for Compounds 2, 3, 4, or 5) and (ii) the selection for substituents $R_1$ through $R_5$ is separate for each individual substituent $R_1$ (silver) can be the same or different element with respect to $R_2$ $R_3$, $R_4$, and $R_5$ (gold, silver, or copper)).

A "ring structure," as used herein, is a ring composed of a hydrocarbon or a substituted hydrocarbon, and the ring structure can be saturated or unsaturated and the ring structure can contain one, or two, or more than two rings.

The "substrate" is a support for the organic light-emitting device. Nonlimiting examples of material suitable for the substrate include quartz plate, glass plate, metal plate, metal foil, plastic film from polymeric resins such as polyester, polymethacrylate, polycarbonate, and polysulfone.

DETAILED DESCRIPTION

1. Composition

The present disclosure provides a composition. The composition includes Compound 1. The structure for Compound 1 is provided below.

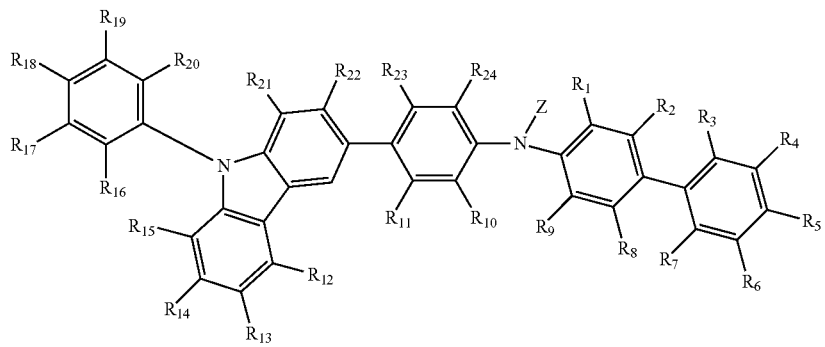

Compound 1

For Compound 1, $R_1$ through $R_{24}$ are the same or different and each of $R_1$ through $R_{24}$ is independently selected from hydrogen, unsubstituted hydrocarbyl, substituted hydrocarbyl, a cyano, alkoxy, aryloxy, and $NR'_2$. Two or more of adjacent $R_1$ to $R_{24}$ may optionally form one or more ring structures.

For the $NR'_2$ moiety of Compound 1, R' is hydrogen or hydrocarbyl.

For Compound 1, Component Z is selected from Group Z-1, Group Z-2, Group Z-3, Group Z-4, Group Z-5, Group Z-6, and Group Z-7. The structures for Groups Z-1, Z-2, Z-3, Z-4, Z-5, Z-6, and Z-7 are provided below:

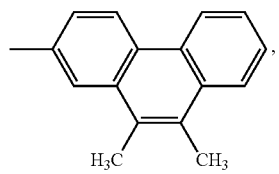

Group Z-1

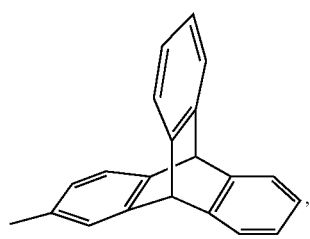

Group Z-2

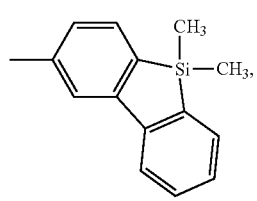

Group Z-3

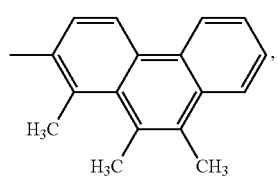

Group Z-4

-continued

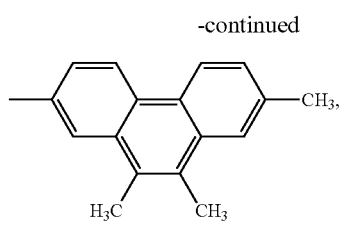

Group Z-5

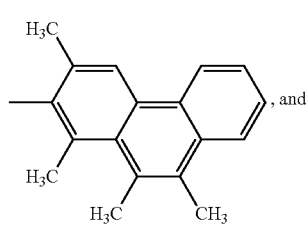

Group Z-6

, and

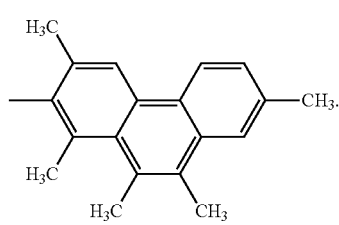

Group Z-7

For Compound 1, one, some, or all hydrogen atoms optionally may be substituted with deuterium.

In an embodiment, Compound 1 includes Group Z-1 (below).

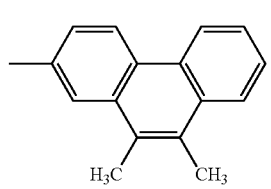

Group Z-1

In an embodiment, Compound 1 includes Group Z-2 (below).

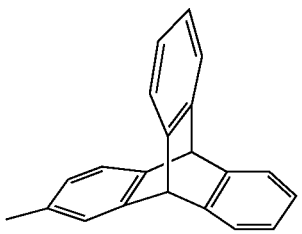

Group Z-2

In an embodiment, Compound 1 includes Group Z-3 (below).

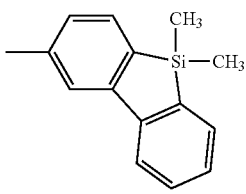

Group Z-3

In an embodiment, Compound 1 includes Group Z-4 (below).

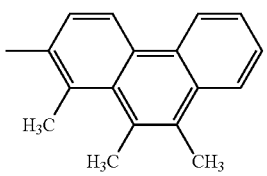

Group Z-4

In an embodiment, Compound 1 includes Group Z-5 (below).

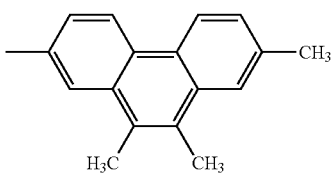

Group Z-5

In an embodiment, Compound 1 includes Group Z-6 (below).

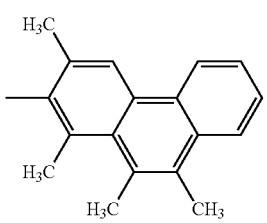

Group Z-6

In an embodiment, Compound 1 includes Group Z-7 (below).

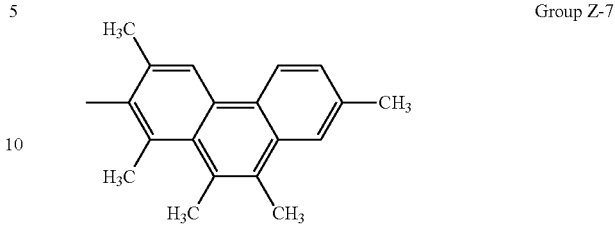

Group Z-7

In an embodiment, Compound 1 has a purity greater than 99 percent (%) as determined by analytical methods, for example, high-performance liquid chromatography (HPLC), liquid chromatography (LC), and/or liquid chromatography-mass spectrometry (LC-MS or HPLC-MS).

In an embodiment, for Compound 1, $R_1$ through $R_{24}$ each is independently selected from following: hydrogen, unsubstituted hydrocarbyl and substituted hydrocarbyl.

In an embodiment, for Compound 1, $R_1$ through $R_{24}$ each is hydrogen.

In an embodiment, Compound 1 has a HOMO level from −4.50 eV, or −4.55 eV, or −4.60 eV to −4.80 eV, or −4.85 eV, or −4.90 eV.

In an embodiment, Compound 1 has a LUMO level from 0.00 eV, or −0.20 eV, or −0.50 eV to −1.00 eV, or −1.05 eV, or −1.10 eV.

In an embodiment, Compound 1 has a triplet energy level from 2.50 eV, or 2.90 eV to 3.10 eV, or 3.30 eV.

In an embodiment, Compound 1 has a molecular weight from 500 grams/mole (g/mol), or 550 g/mol, or 600 g/mol, or 650 g/mol, or 700 g/mol to 800 g/mol, or 850 g/mol, or 900 g/mol, or 950 g/mol, or 1000 g/mol.

In an embodiment, Compound 1 has a Tg from 110° C., or 120° C., or 130° C., or 140° C., or 150° C. to 160° C., or 170° C., or 180° C., as determined by DSC.

A. Group Z-1

In an embodiment, the composition includes Compound 1, and $R_1$ through $R_{24}$ each is independently selected from hydrogen, unsubstituted hydrocarbyl, and substituted hydrocarbyl. Component Z for Compound 1 includes Group Z-1 as shown below:

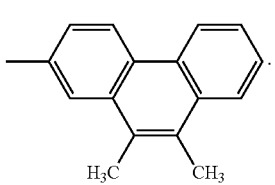

Group Z-1

In an embodiment, Compound 1 with Group Z-1 has a molecular weight (MW) from 690 g/mole to 900 g/mole.

In an embodiment, the composition includes Compound 1 with Group Z-1, and Compound 1 has the Structure (i) below:

Structure (i)

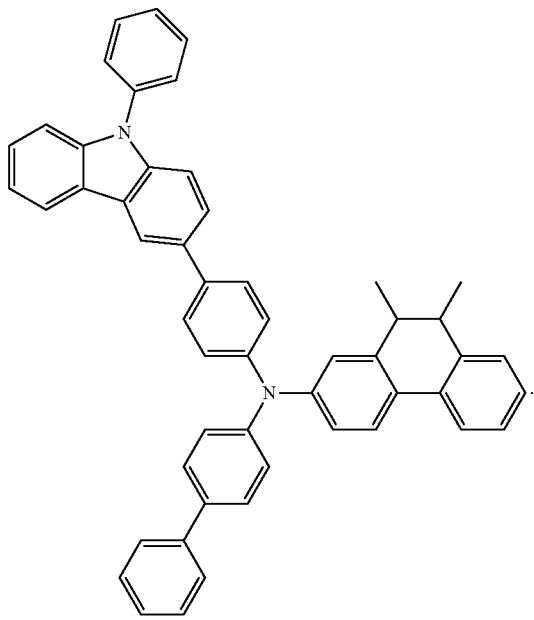

In an embodiment, Structure (i) has a HOMO level from −4.50 eV to −4.90 eV.

In an embodiment, Structure (i) has a LUMO level from 0.00 eV to −1.10 eV.

In an embodiment, Structure (i) has a triplet energy level from 2.50 eV to 3.30 eV.

In an embodiment, the Structure (i) has a glass transition temperature, Tg, from 110° C. to 180° C., as determined by DSC.

B. Group Z-2

In an embodiment, the composition includes Compound 1, and $R_1$ through $R_{24}$ each is independently selected from hydrogen, unsubstituted hydrocarbyl, and substituted hydrocarbyl. Component Z for Compound 1 is Group Z-2 below:

Group Z-2

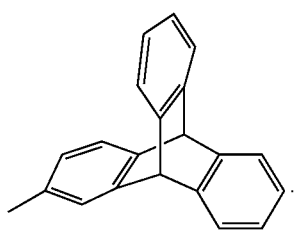

In an embodiment, Compound 1 with Group Z-2 has a molecular weight from 738 g/mole to 900 g/mole.

In an embodiment, the composition includes Compound 1 with Group Z-2, and Compound 1 has the Structure (ii) below:

Structure (ii)

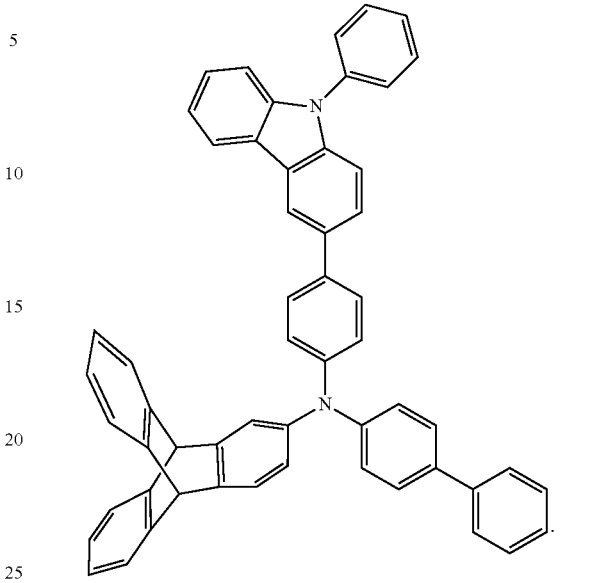

In an embodiment, Structure (ii) has a HOMO level from −4.50 eV to −4.90 eV.

In an embodiment, Structure (ii) has a LUMO level from 0.00 eV to −1.10 eV.

In an embodiment, Structure (ii) has a triplet energy level from 2.50 eV to 3.30 eV.

In an embodiment, the Structure (ii) has a glass transition temperature, Tg, from 110° C. to 180° C., as determined by DSC.

C. Group Z-3

In an embodiment, the composition includes Compound 1, and $R_1$ through $R_{24}$ each is independently selected from hydrogen, unsubstituted hydrocarbyl, and substituted hydrocarbyl. Component Z for Compound 1 is Group Z-3 below:

Group Z-3

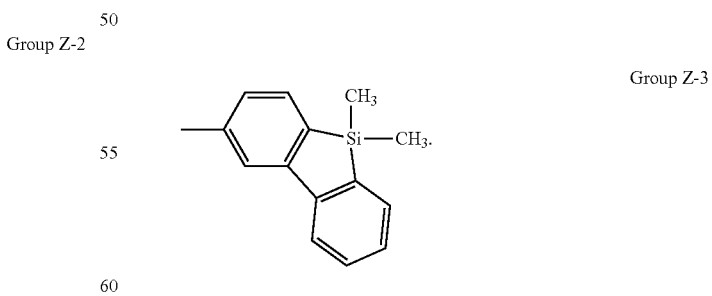

In an embodiment, Compound 1 with Group Z-3 has a molecular weight from 694 g/mole to 900 g/mole.

In an embodiment, the composition includes Compound 1 with Group Z-3, and Compound 1 has the Structure (iii) below:

Structure (iii)

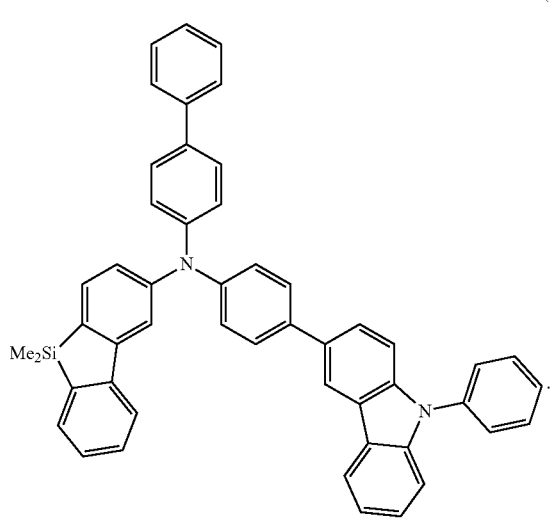

In an embodiment Structure (iii) has a HOMO level from −4.50 eV to −4.90 eV.

In an embodiment, structure (iii) has a LUMO level from 0.00 eV to −1.10 eV.

In an embodiment, Structure (iii) has a triplet energy level from 2.50 eV to 3.30 eV.

In an embodiment, the Structure (iii) has a glass transition temperature, Tg, from 110° C. to 180° C., as determined by DSC.

D. Group Z-4

In an embodiment, the composition includes Compound 1, and $R_1$ through $R_{24}$ each is independently selected from hydrogen, unsubstituted hydrocarbyl, and substituted hydrocarbyl. Component Z for Compound 1 is Group Z-4 below:

Group Z-4

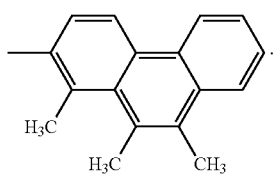

In an embodiment, Compound 1 with Group Z-4 has a molecular weight from 694 g/mole to 900 g/mole.

In an embodiment, Compound 1 with Group Z-4 has a HOMO level from −4.50 eV to −4.90 eV.

In an embodiment, Compound 1 with Group Z-4 has a LUMO level from 0.00 eV to −1.10 eV.

In an embodiment, Compound 1 with Group Z-4 has a triplet energy level from 2.50 eV to 3.30 eV.

In an embodiment, Compound 1 with Group Z-4 has a glass transition temperature, Tg, from 110° C. to 180° C., as determined by DSC.

E. Group Z-5

In an embodiment, the composition includes Compound 1, and $R_1$ through $R_{24}$ each is independently selected from hydrogen, unsubstituted hydrocarbyl, and substituted hydrocarbyl. Component Z for Compound 1 is Group Z-5 below:

Group Z-5

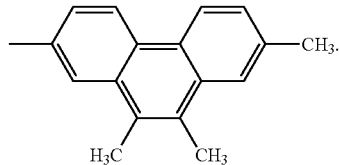

In an embodiment, Compound 1 with Group Z-5 has a molecular weight from 694 g/mole to 900 g/mole.

In an embodiment, Compound 1 with Group Z-5 has a HOMO level from −4.50 eV to −4.90 eV.

In an embodiment, Compound 1 with Group Z-5 has a LUMO level from 0.00 eV to −1.10 eV.

In an embodiment, Compound 1 with Group Z-5 has a triplet energy level from 2.50 eV to 3.30 eV.

In an embodiment, Compound 1 with Group Z-5 has a glass transition temperature, Tg, from 110° C. to 180° C., as determined by DSC.

F. Group Z-6

In an embodiment, the composition includes Compound 1, and $R_1$ through $R_{24}$ each is independently selected from hydrogen, unsubstituted hydrocarbyl, and substituted hydrocarbyl. Component Z for Compound 1 is Group Z-6 below:

Group Z-6

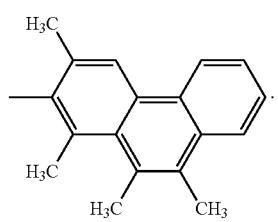

In an embodiment, Compound 1 with Group Z-6 has a molecular weight from 694 g/mole to 900 g/mole.

In an embodiment, Compound 1 with Group Z-6 has a HOMO level from −4.50 eV to −4.90 eV.

In an embodiment, Compound 1 with Group Z-6 has a LUMO level from 0.00 eV to −1.10 eV.

In an embodiment, Compound 1 with Group Z-6 has a triplet energy level from 2.50 eV to 3.30 eV.

In an embodiment, Compound 1 with Group Z-6 has a glass transition temperature, Tg, from 110° C. to 180° C., as determined by DSC.

G. Group Z-7

In an embodiment, the composition includes Compound 1, and $R_1$ through $R_{24}$ each is independently selected from hydrogen, unsubstituted hydrocarbyl, and substituted hydrocarbyl. Component Z for Compound 1 is Group Z-7 below:

Group Z-7

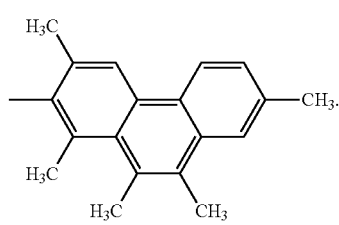

In an embodiment, Compound 1 with Group Z-7 has a molecular weight from 694 g/mole to 900 g/mole.

In an embodiment, Compound 1 with Group Z-7 has a HOMO level from −4.50 eV to −4.90 eV.

In an embodiment, Compound 1 with Group Z-7 has a LUMO level from 0.00 eV to −1.10 eV.

In an embodiment, Compound 1 with Group Z-7 has a triplet energy level from 2.50 eV to 3.30 eV.

In an embodiment, Compound 1 with Group Z-7 has a glass transition temperature, Tg, from 110° C. to 180° C., as determined by DSC.

In an embodiment, one, some, or all methyl moieties on Groups Z-1 through Z-7 may be replaced by, or otherwise substituted with, an alkyl containing 2, 3, 4, 5, or 6 carbon atoms.

The present composition may comprise two or more embodiments disclosed herein.

Compound 1 may comprise two or more embodiments disclosed herein.

2. Film

The present disclosure provides a film. The film includes, or is otherwise formed from, the present composition.

In an embodiment, the film includes the composition composed of Compound 1. Compound 1 can have any structure previously disclosed herein.

In an embodiment, the film includes the composition composed of Compound 1. Component Z of Compound 1 is Group Z-1.

In an embodiment, the film includes the composition composed of Compound 1. Component Z of Compound 1 is Group Z-2.

In an embodiment, the film includes the composition composed of Compound 1. Component Z of Compound 1 is Group Z-3.

In an embodiment, the film includes the composition composed of Compound 1. Component Z of Compound 1 is Group Z-4.

In an embodiment, the film includes the composition composed of Compound 1. Component Z of Compound 1 is Group Z-5.

In an embodiment, the film includes the composition composed of Compound 1. Component Z of Compound 1 is Group Z-6.

In an embodiment, the film includes the composition composed of Compound 1. Component Z of Compound 1 is Group Z-7.

In an embodiment, the film includes the composition composed of one or more Compound 1s, the plurality of Compound 1s having two or more different Z components selected from Group Z-1, Group Z-2, Group Z-3, Group Z-4, Group Z-5, Group Z-6, and Group Z-7 and any combination thereof.

In an embodiment, the film is formed with an evaporative process.

In an embodiment, the film is formed in a solution process.

The present film may comprise two or more embodiments disclosed herein.

3. Device

The present disclosure provides an electronic device. The electronic device includes at least one component that includes, or is otherwise formed from, the present composition.

In an embodiment, the electronic device includes the composition composed of Compound 1. Compound 1 can have any structure previously disclosed herein.

In an embodiment, the electronic device includes the composition composed of Compound 1. Component Z of Compound 1 is Group Z-1.

In an embodiment, the electronic device includes the composition composed of Compound 1. Component Z of Compound 1 is Group Z-2.

In an embodiment, the electronic device includes the composition composed of Compound 1. Component Z of Compound 1 is Group Z-3.

In an embodiment, the electronic device includes the composition composed of Compound 1. Component Z of Compound 1 is Group Z-4

In an embodiment, the electronic device includes the composition composed of Compound 1. Component Z of Compound 1 is Group Z-5.

In an embodiment, the electronic device includes the composition composed of Compound 1. Component Z of Compound 1 is Group Z-6.

In an embodiment, the electronic device includes the composition composed of Compound 1. Component Z of Compound 1 is Group Z-7.

In an embodiment, the electronic device includes the composition composed two or more Compound 1s, the plurality of Compound 1s having two or more different Z components selected from Group Z-1, Group Z-2, Group Z-3, Group Z-4, Group Z-5, Group Z-6, and Group Z-7 and any combination thereof.

In an embodiment, the electronic device is an organic light-emitting diode (OLED) device. The present composition can be present in one, some, or all of the following layers: hole injection layer (HIL), a hole transport layer (HTL), an emitting material layer (EML), an electron transport layer (ETL), and an electron injection layer (EIL). As a layer, the present composition has a layer thickness from 5 nanometers (nm), or 10 nm, or 20 nm, or 25 nm to 30 nm, or 35 nm, or 40 nm, or 50 nm, or 60 nm, or 70 nm, or 80 nm, or 90 nm.

In an embodiment, the electronic device is an OLED device and the present composition is present in the hole transport layer (HTL) and the HTL has a thickness from 5 nanometers (nm), or 10 nm, or 20 nm, or 25 nm to 30 nm, or 35 nm, or 40 nm, or 50 nm, or 60 nm, or 70 nm, or 80 nm, or 90 nm.

The present electronic device may comprise a combination of two or more embodiments disclosed herein.

Some embodiments of the present disclosure will now be described in detail in the following Examples.

Examples

1. Reagents and Test Methods

All solvents and reagents are obtained from commercial vendors, including Sigma-Aldrich, TCI, and Alfa Aesar, and are used in the highest available purities, and/or when necessary, recrystallized before use. Dry solvents are obtained from in-house purification/dispensing system (hexane, toluene, and tetrahydrofuran), or purchased from Sigma-Aldrich. All experiments involving "water sensitive compounds" are conducted in "oven dried" glassware, under nitrogen atmosphere, or in a glovebox. Reactions are monitored by analytical, thin-layer chromatography (TLC) on precoated glass plates (VWR 60 F254), and visualized by UV light and/or potassium permanganate staining. Flash chromatography is performed on an ISCO COMBIFLASH system with GRACERESOLV cartridges. GC-mass spectrometry (GC-MS) is performed on a HP 6890 series GC system with a "12 m×0.2 mm×0.55 µM" DB-MS column (coiled).

$^1$H-NMR-spectra (500 MHz or 400 MHz) are obtained on a Varian VNMRS-500 or a VNMRS-400 spectrometer, at 30° C., unless otherwise noted. The chemical shifts are referenced to TMS (δ=0.00) in CDCl$_3$.

$^{13}$C-NMR spectra (125 MHz or 100 MHz) are obtained on a Varian VNMRS-500 or a VNRMS-400 spectrometer, and referenced to TMS (δ=0.00) in CDCl$_3$.

Routine LC/MS studies are carried out as follows. Five microliter aliquots of the sample, as "3 mg/ml solution in THF," are injected on an AGILENT 1200SL binary gradient, liquid chromatography, coupled to an AGILENT 6520 QTof, quadruple-time of flight MS system, via a dual spray electrospray (ESI) interface, operating in the PI mode. The following analysis conditions are used: column: 150×4.6 mm ID, 3.5 µm ZORBAX SB-C8; column temperature: 40° C.; mobile phase: 75/25 A/B to 15/85 A/B at 40 minutes; solvent A=0.1 v % formic acid in water; solvent B=THF; flow 1.0 mL/min; UV detection: diode array 210 to 600 nm (extracted wavelength 250,280 nm); ESI conditions: gas temperature 365° C.; gas flow—8 ml/min; capillary—3.5 kV; nebulizer—40 PSI; fragmentor—145V.

DSC is performed using a 2000 instrument at a scan rate of 10° C./min, and in a nitrogen atmosphere for all cycles. The sample (about 7-10 mg) is scanned from room temperature to 300° C., cooled to −60° C., and reheated to 300° C. The glass transition temperature ($T_g$) is measured on the second heating scan. Data analysis is performed using TA Universal Analysis software. The $T_g$ is calculated using the "mid-point of inflection" methodology.

2. Modeling

All computations utilize the Gaussian09 program[1]. The calculations are performed with the hybrid density functional theory (DFT) method, B3LYP,[2] and the 6-31G* (5d) basis set.[3] The singlet state calculations use the closed shell approximation, and the triplet state calculations use the open shell approximation. The HOMO and LUMO values are determined from the orbital energies of the optimized geometry of the singlet ground state, and this energy is denoted as $E_{S0}(S_0)$. The Triplet Energy ($T_1$) is the difference between the total energy of the optimized triplet state and the optimized singlet state.

[1] Gaussian 09, Revision A.02, Frisch, M. J.; Trucks, G. W.; Schlegel, H. B.; Scuseria, G. E.; Robb, M. A.; Cheeseman, J. R.; Scalmani, G.; Barone, V.; Mennucci, B.; Petersson, G. A.; Nakatsuji, H.; Caricato, M.; Li, X.; Hratchian, H. P.; Izmaylov, A. F.; Bloino, J.; Zheng, G.; Sonnenberg, J. L.; Hada, M.; Ehara, M.; Toyota, K.; Fukuda, R.; Hasegawa, J.; Ishida, M.; Nakajima, T.; Honda, Y.; Kitao, O.; Nakai, H.; Vreven, T.; Montgomery, Jr., J. A.; Peralta, J. E.; Ogliaro, F.; Bearpark, M.; Heyd, J. J.; Brothers, E.; Kudin, K. N.; Staroverov, V. N.; Kobayashi, R.; Normand, J.; Raghavachari, K.; Rendell, A.; Burant, J. C.; Iyengar, S. S.; Tomasi, J.; Cossi, M.; Rega, N.; Millam, J. M.; Klene, M.; Knox, J. E.; Cross, J. B.; Bakken, V.; Adamo, C.; Jaramillo, J.; Gomperts, R.; Stratmann, R. E.; Yazyev, O.; Austin, A. J.; Cammi, R.; Pomelli, C.; Ochterski, J. W.; Martin, R. L.; Morokuma, K.; Zakrzewski, V. G.; Voth, G. A.; Salvador, P.; Dannenberg, J. J.; Dapprich, S.; Daniels, A. D.; Farkas, O.; Foresman, J. B.; Ortiz, J. V.; Cioslowski, J.; Fox, D. J., Gaussian, Inc., Wallingford Conn., 2009.

[2] (a) Becke, A. D. *J. Chem. Phys.* 1993, 98, 5648. (b) Lee, C.; Yang, W.; Parr, R. G. *Phys. Rev B* 1988, 37, 785. (c) Miehlich, B.; Savin, A.; Stoll, H.; Preuss, H. *Chem. Phys. Lett.* 1989, 157, 200.

[3] (a) Ditchfield, R.; Hehre, W. J.; Pople, J. A. *J. Chem. Phys.* 1971, 54, 724. (b) Hehre, W. J.; Ditchfield, R.; Pople, J. A. *J. Chem. Phys.* 1972, 56, 2257. (c) Gordon, M. S. *Chem. Phys. Lett.* 1980, 76, 163.

The estimation of h-mobility (λ+) is performed by a stepwise process. First, the geometry of the HTL molecule is optimized in the radical cation state $E_{cat}(Cat)$. In the next step, the energy of the radical cation is obtained in the singlet ground state geometry, $E_{cat}(S_0)$. In the third step, the energy of singlet state is obtained in the radical cation geometry, $E_{S0}(Cat)$. The h-mobility (λ+) is estimated using the following equation;

$$\lambda+ = (E_{cat}(S_0) - E_{cat}(Cat)) + (E_{S0}(Cat) - E_{S0}(S_0))$$

All values are quoted in electronvolts (eV).

HOMO, LUMO, Triplet, and H-mobility values are calculated by B3LYP/6-31G* method and are shown in Table 1 below.

TABLE 1

| Component Z | HOMO (eV) | LUMO (eV) | $T_1$ (eV) | h-mobility (λ + eV) | MW |
|---|---|---|---|---|---|
| Structure (i) (Z-1) | −4.73 | −0.92 | 2.64 | 0.18 | 690.87 |
| Structure (ii) (Z-2) | −4.70 | −0.77 | 2.66 | 0.18 | 738.93 |
| Structure (iii) (Z-3) | −4.76 | −0.96 | 2.67 | 0.22 | 694.95 |
| Structure (Z-4) | −4.76 | −1.00 | 2.45 | 0.19 | 704.92 |
| Structure (Z-5) | −4.70 | −0.90 | 2.65 | 0.18 | 704.92 |
| Structure (Z-6) | −4.78 | −0.96 | 2.69 | 0.20 | 718.33 |
| Structure (Z-7) | −4.76 | −0.94 | 2.69 | 0.20 | 732.97 |

3. Synthesis

A. Synthesis of HTL with Structure (i)

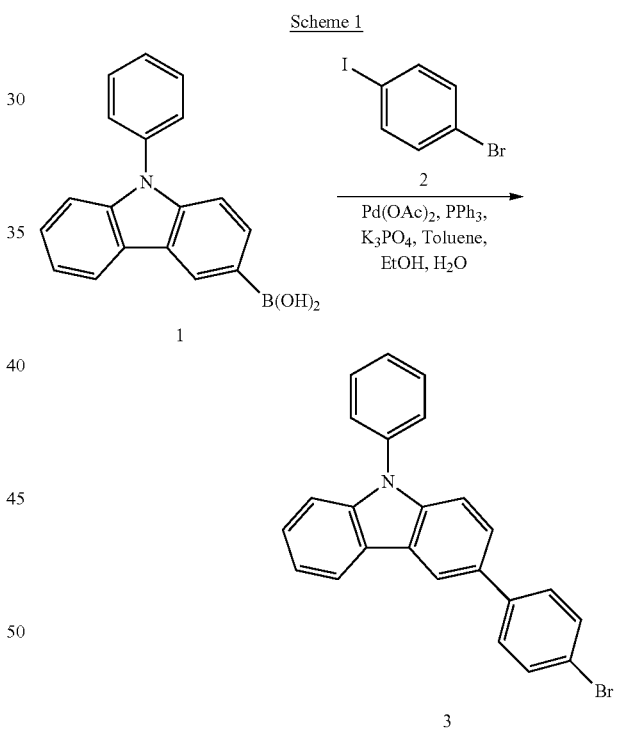

Scheme 1

A 3 necked 500 mL round bottomed flask, equipped with a stir bar, a thermocouple, and a water condenser, and with nitrogen inlet, is charged with phenyl carbazole boronic acid 1 (9.5 g, 33.06 mmol), 1-iodo-4-bromobenzene (9.37 g, 33.12 mmol), palladium acetate (0.139 g, 0.62 mmol), triphenyl phosphine (0.449 g, 1.71 mmol), and toluene 140 mL). Then 44 g of "40% (w/w) potassium phosphate tribasic diluted with water (46 mL) and ethanol (46 mL)" is added, and the reaction heated to 75° C. (reflux). After 2 hours (h), the reaction is allowed to cool to room temperature, and the mixture is extracted with ethyl acetate. The combined organic layers are dried over magnesium sulfate, filtered, and concentrated. The crude material is purified on the combiflash (hexane/5% ethyl acetate) to give approximately 9 g of product. The material is dissolved in toluene (30 mL), and is precipitated with hexanes (90 mL) (solids started to form after 60 mL added). The precipitate is isolated by vacuum filtration, to give pure product 3 (8.3 g, 20.8 mmol, 63%).

$^1$H NMR (400 MHz, Chloroform-d) δ 8.30 (dd, J=1.8, 0.7 Hz, 1H), 8.18 (dt, J=7.8, 1.0 Hz, 1H), 7.65-7.54 (m, 9H), 7.51-7.39 (m, 4H), 7.31 (ddd, J=8.0, 5.2, 3.0 Hz, 1H).

$^{13}$C NMR (101 MHz, CDCl$_3$) δ 141.42, 140.94, 140.54, 137.56, 132.16, 131.83, 129.95, 128.88, 127.62, 127.08, 126.28, 125.16, 123.95, 123.34, 120.71, 120.37, 120.17, 118.64, 110.15, 109.99.

Scheme 2

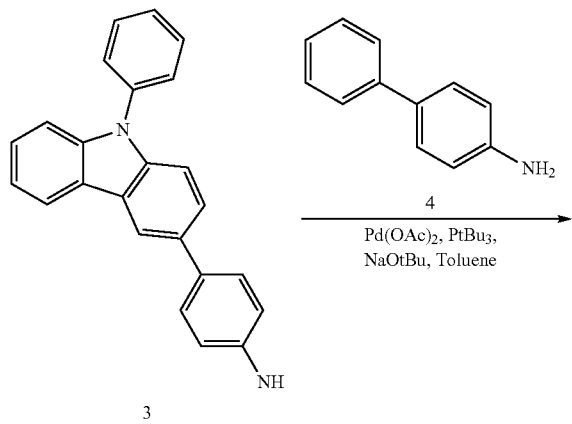

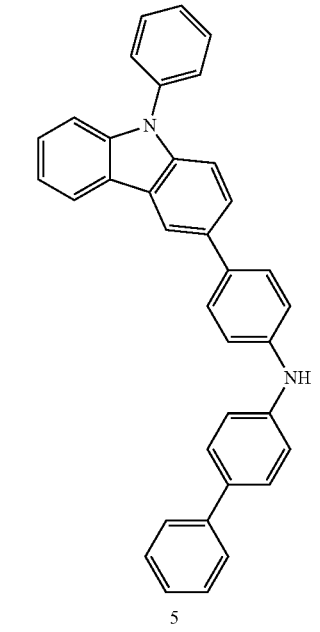

A 250 mL three necked round bottomed flask equipped with a stir bar, thermocouple, heating mantle, and water condenser, and with nitrogen inlet is charged with 3-(4-bromophenyl)-N-phenylcarbazole 3 (4.46 g, 11.2 mmol), 4-aminobiphenyl (2.11 g, 12.5 mmol), sodium t-butoxide (2.18 g, 22.7 mmol) and palladium acetate (0.053 g, 0.24 mmol) and the flask is purged with nitrogen for 5 minutes. Toluene (67 mL) that has been degassed with nitrogen for 5 minutes is added followed by tri-tert-butylphosphine (0.120 g, 0.6 mmol) dissolved in toluene (3 mL) and the reaction heated to 110° C. (start time: 5 PM). After 16.5 hours (h), HPLC showed very little conversion to product so more sodium t-butoxide (1.0 g) is added followed by Pd(dppf)Cl$_2$ chloroform adduct (0.20 g). After 39 h the reaction is cooled to room temperature and partitioned between water and ethyl acetate. The aqueous layer is extracted with ethyl acetate and the combined organic layers are dried over magnesium sulfate, filtered, and concentrated. The crude material is dissolved in methylene chloride and concentrated onto ~40 g of silica gel and purified on the combiflash (0 to 30% methylene chloride/hexanes). Fractions 36-60 are collected to provide the titled compound (5) in 97% purity (3.22 g, 6.62 mmol, 59%).

$^1$H NMR (400 MHz, Chloroform-d) δ 8.32 (dd, J=1.8, 0.7 Hz, 1H), 8.18 (dt, J=7.7, 1.0 Hz, 1H), 7.69-7.50 (m, 11H), 7.50-7.37 (m, 6H), 7.36-7.26 (m, 2H), 7.25-7.14 (m, 4H), 5.82 (s, 1H).

$^{13}$C NMR (101 MHz, CDCl$_3$) δ 141.35, 137.74, 129.91, 128.75, 127.47, 127.09, 126.61, 126.09, 123.53, 120.36, 120.02, 109.92.

Scheme 3

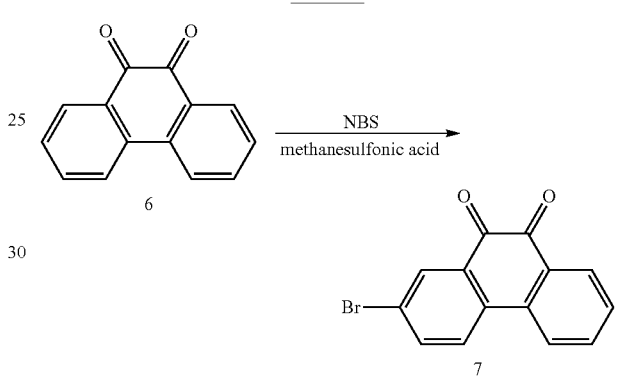

Phenanthrenequinone (5.77 g; 27.7 mmol) is dissolved in 80 mL of methanesulfonic acid in a 250 mL round-bottomed flask. N-bromosuccinimide (NBS) (4.93 g; 27.7 mmol) is added slowly in small portions over a period of 30 min. The solution is stirred at room temperature overnight. It is then poured into a mixture of ice and water to terminate this reaction and an orange precipitate forms. The orange precipitate is dissolved in CH$_2$Cl$_2$ and then washed with an aqueous solution of saturated sodium bicarbonate. The solvent is removed under reduced pressure, and the product is purified by column chromatography (50-70% methylene chloride/hexane gradient) to afford Compound 7 (Yield is 44.0%).

Scheme 4

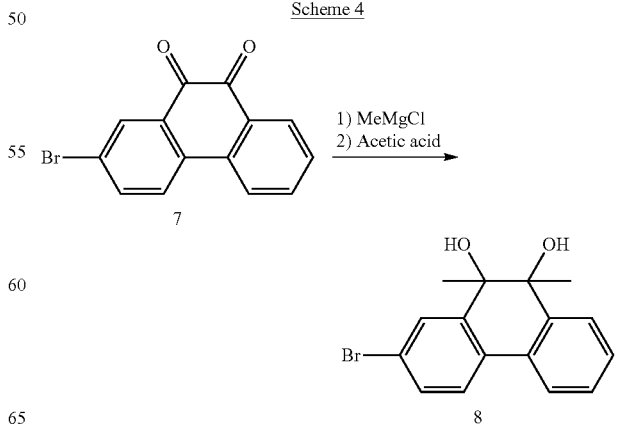

Compound 7 (8 g) is suspended in THF (250 mL) and MeMgCl (37.2 mL of a 3 M in THF) is added. The mixture is stirred overnight at 50° C. and glacial acetic acid (20 mL) is added under ice cooling and the solution is diluted with EtOAc. After washing twice with saturated NaCl solution, the solution is dried over $Na_2SO_4$ and solvent is removed under vacuum (Yield is 90.0%).

Scheme 5

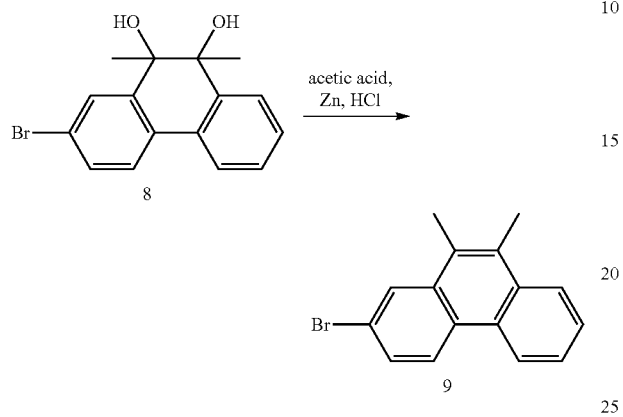

Compound 8 (8 g, 25.04 mmole) is dissolved in glacial acetic acid (400 mL) and the mixture is heated at 130° C. for 30 min. To the mixture, Zn (8.08 g) is added slowly, which is followed by the slow addition of HCl (12 M, 8 mL). After 30 minutes another addition of Zn (8 g) is added along with HCl (12 M, 8 mL). The mixture is refluxed for 12 h and upon cooling to room temp and the addition of water (500 mL) a solid is formed. The solid is isolated upon filteration and it is washed with a NaOH solution and is purified by column chromatography (100% hexane) (Yield is 64.9%).

$^1$H NMR (400 MHz, chloroform-d) δ ppm 2.67 (s, 3H) 2.71 (s, 3H) 7.56-7.68 (m, 3H) 8.09 (d, J=7.63 Hz, 1H) 8.22 (s, 1H) 8.53 (d, J=8.80 Hz, 1H) 8.62 (d, J=7.82 Hz, 1H)

Scheme 6

Structure (i)

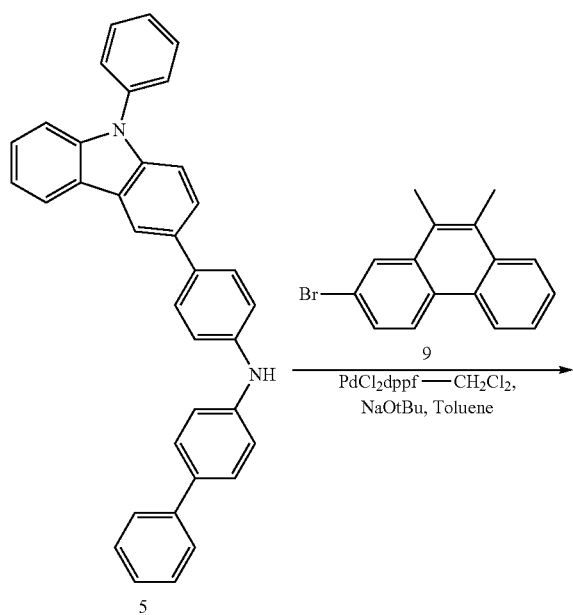

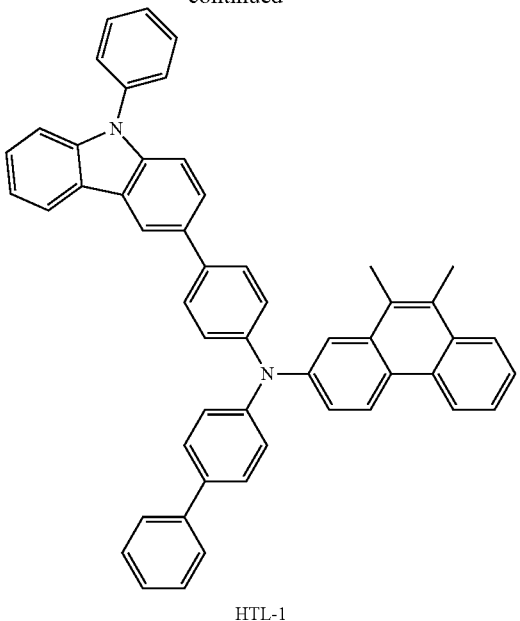

HTL-1

The reaction is undertaken in a nitrogen dry box. A 100 mL round bottomed flask is charged with 5 (1.2 g, 2.46 mmol), 9 (0.70 g, 2.46 mmol), NaOtBu (0.355 g, 3.7 mmol), Pd(dppf)Cl$_2$ (0.040 g, 0.049 mmol), and toluene (50 mL). The mixture is stirred at 110° C. overnight. An aliquot is removed and analysis by GC-MS and NMR spectroscopy shows that the reaction is complete. The reaction is allowed to cool and is treated with EtOAc (200 mL) and water (200 mL). The organic layer is isolated, dried with MgSO$_4$, and is filtered. The solvent is removed under reduced pressure to afford crude structure (i). It is purified by column chromatography using the Biotage with a mixed solvent of CH$_2$Cl$_2$ and hexane. The solvent profile is increased to 25% CH$_2$Cl$_2$ over 6 column lengths and this ratio is until structure (i) elutes. Yield is 1.2 g (70%).

$^1$H NMR (400 MHz, C$_6$D$_6$) δ 8.55 (d, J=9.0 Hz, 1H), 8.54-8.50 (m, 1H), 8.44 (d, J=1.7 Hz, 1H), 8.20 (d, J=2.3 Hz, 1H), 8.12 (d, J=6.9 Hz, 1H), 7.99-7.91 (m, 1H), 7.68 (d, J=8.6 Hz, 3H), 7.59 (dd, J=8.9, 2.3 Hz, 1H), 7.56-7.50 (m, 4H), 7.45 (d, J=6.5 Hz, 7H), 7.38-7.18 (m, 10H), 7.08 (d, J=7.2 Hz, 1H), 2.37 (s, 3H), 2.28 (s, 3H).

$^{13}$C NMR (101 MHz, C$_6$D6) δ 147.94, 147.09, 146.70, 141.93, 141.17, 140.80, 138.15, 137.53, 136.05, 134.24, 133.59, 132.32, 130.28, 130.12, 130.02, 129.23, 129.14, 128.79, 128.46, 128.30, 128.18, 128.17, 127.45, 127.36, 127.16, 127.11, 126.53, 126.53, 126.31, 126.21, 125.97, 125.69, 125.40, 125.07, 124.83, 124.68, 124.56, 124.20, 123.58, 123.03, 120.86, 120.57, 119.51, 119.01, 110.49, 110.31, 15.91, 15.89.

B. Synthesis for HTL with Structure (ii)

Scheme 7

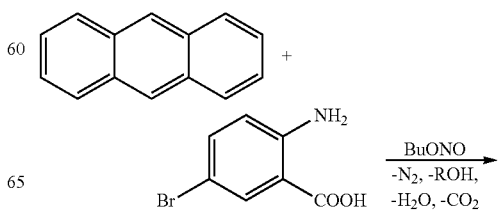

-continued

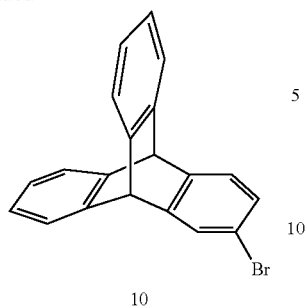

10

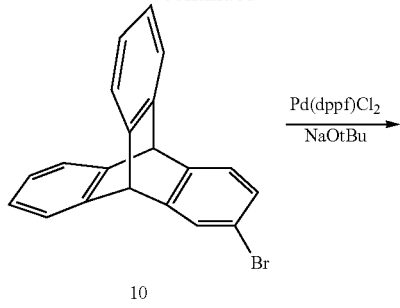

10

The anthranilic acid (3.62 g; 16.9 mmol) is added to a 500 mL round-bottomed flask and MeCN (400 mL) is added. The mixture is heated to 50° C. and rapidly stirred. This slurry is added drop wise to a solution of anthracene (6.0 g; 33.7 mmol) in MeCN (300 mL) that is heated to just below its reflux. Concurrently, a solution of the BuONO (4.9 mL) in MeCN (400 mL) is also added. The addition is carried out over 3 hours. The reaction cooled to room temperature and ca. 90% of the solvent is removed on a roto yap. The mixture is filtered and 3.9 grams of anthracene is isolated. The mother liquor is analyzed and shown to contain 2-bromotriptycene. It is treated with $CH_2Cl_2$ (200 mL) and water (200 mL). The organic layer is isolated, dried with $MgSO_4$, and filtered. 3.3 g of a sticky yellow brown solid is obtained upon removing the solvent. It is purified by column chromatography (0-20% $CH_2Cl_2$ in hexane) and Compound 10 (0.9 g; 16% yield) is obtained as a colorless solid. $^1$H NMR (400 MHz, Chloroform-d) δ 7.52 (d, J=1.9 Hz, 1H), 7.37 (dd, J=5.4, 3.2 Hz, 4H), 7.29-7.19 (m, 2H), 7.11 (dd, J=7.8, 1.9 Hz, 1H), 7.00 (d, J=8.5 Hz, 4H), 5.38 (d, J=5.9 Hz, 2H); $^{13}$C NMR (101 MHz, Chloroform-d) δ 147.75, 144.91, 144.64, 144.62, 128.05, 127.02, 125.57, 125.53, 125.20, 123.91, 123.83 118.66, 53.84, 53.67.

Scheme 8

Structure (ii)

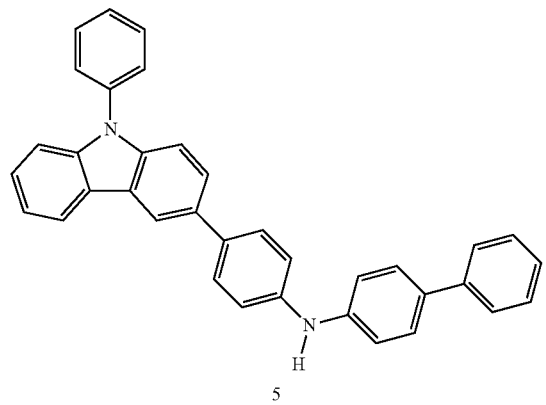

5

+

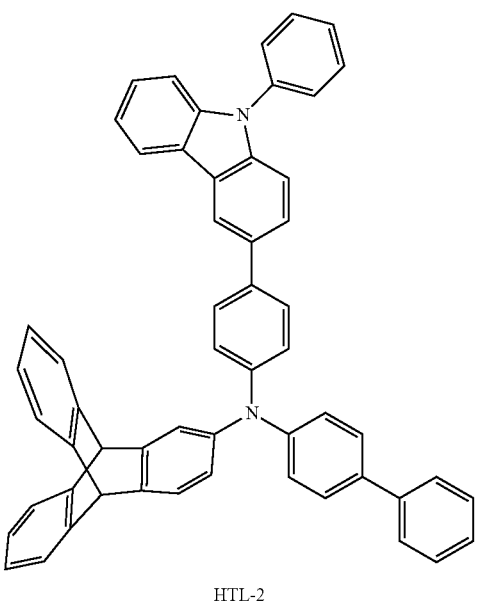

HTL-2

The reaction is undertaken in a nitrogen dry box. A 100 mL round bottomed flask is charged with Compound 5 (1.45 g, 2.97 mmol), Compound 10 (0.899 g, 2.70 mmol), NaOtBu (0.390 g, 4.06 mmol), Pd(dppf)Cl$_2$ (0.044 g, 0.054 mmol), and toluene (100 mL). The mixture is stirred at 110° C. overnight. An aliquot is removed and analysis by GC-MS and NMR spectroscopy shows that the reaction is complete. The reaction is allowed to cool and is treated with EtOAc (200 mL) and water (200 mL). The organic layer is isolated, dried with $MgSO_4$, and is filtered. The solvent is removed under reduced pressure to afford crude HTL-2. It is purified by column chromatography using the Biotage with a mixed solvent of $CH_2Cl_2$ and hexane. The solvent profile is increased to 40% $CH_2Cl_2$ over 6 column lengths and this ratio is used until HTL-2 eluted. Yield is 1.5 g (75.2%).

$^1$H NMR (400 MHz, Chloroform-d) δ 8.32 (d, J=1.7 Hz, 1H), 8.21-8.14 (m, 1H), 7.66-7.54 (m, 9H), 7.50-7.37 (m, 9H), 7.41-7.24 (m, 6H), 7.25 (d, J=3.0 Hz, 3H), 7.19-7.09 (m, 4H), 7.06-6.98 (m, 4H), 6.81 (dd, J=7.9, 2.2 Hz, 1H), 5.40 (s, 1H), 5.33 (s, 1H);

$^{13}$C NMR (101 MHz, CDCl$_3$) δ 147.30, 146.47, 145.55, 145.24, 144.77, 140.68, 140.07, 137.70, 136.26, 132.98, 129.90, 128.73, 127.91, 127.70, 127.47, 127.06, 126.75, 126.63, 126.08, 125.21, 125.14, 125.07, 124.63, 124.22, 123.87, 123.71, 123.49, 121.08, 120.35, 120.03, 118.31, 110.00, 109.91, 54.08, 53.55.

C. Synthesis for Structure (iii)

Scheme 9

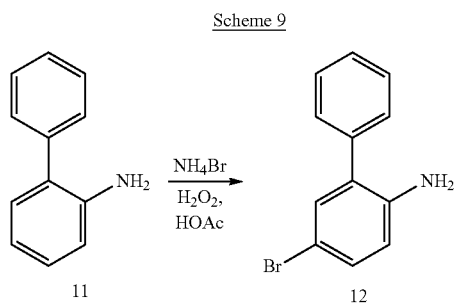

In a 500 mL round bottomed flask, compound 11 (25 g, 147.7 mmoles) and ammonium bromide (15.9 g, 162.5 mmol) are dissolved in glacial acetic acid (300 mL). Using a syringe pump, a 30% solution of $H_2O_2$ (18.1 mL) is added over 2 h. The mixture is allowed to stir overnight and is then quenched by carefully adding a saturated solution of $Na_2CO_3$ and the mixture is extracted with methylene chloride (1 L). The organic layer is dried with $MgSO_4$ and filtered. The crude mixture is purified by chromatography over silica gel using hexane/methylene chloride (4:1) to afford 12 as a colorless solid (65% yield 23.8 g).

$^1$H NMR (400 MHz, CDCl$_3$) δ: 7.49-7.39 (m, 4H), 7.39-7.33 (m, 1H), 7.28-7.18 (m, 1H), 6.73-6.54 (m, 1H), 3.75 (s, 2H).

$^{13}$C NMR (101 MHz, CDCl$_3$) δ: 142.62, 138.15, 132.76, 131.04, 129.38, 128.95, 128.89, 127.66, 117.03, 110.15.

Scheme 10

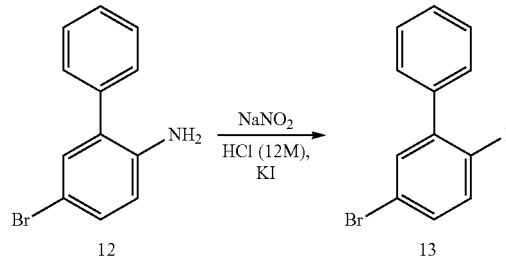

Compound 12 is added to a stirred solution of 12 M HCl (1.7 mL) and water (25 mL) in a 50 mL round bottom flask. The flask is cooled to 0° C. on an ice bath and a solution of NaNO$_2$ [1.23 g dissolved in water (5 mL)] is added dropwise over 5 min. The slurry is stirred for 30 min and then added to a cooled (0° C.) solution of KI (20 mL of water). After the initial vigorous reaction the solution is heated to 50° C. The mixture is extracted with CH$_2$Cl$_2$ and purified by column chromatography to afford 13 as a colorless solid.

Scheme 11

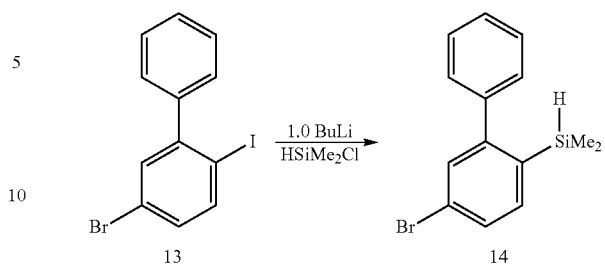

A solution of Compound 13 (3 g) in THF (60 mL) is cooled to −78° C. and n-BuLi is added drop-wise under an atmosphere of nitrogen. After 15 minutes dimethylchlorosilane is added drop-wise at −78° C. and the mixture is warmed to 25° C. slowly. After stirring overnight, a saturated solution of NH$_4$Cl in water is added and the mixture extracted with diethyl ether (360 mL). The organic layer is dried over anhydrous MgSO$_4$, filtered, and concentrated under reduced pressure. The product is isolated by column chromatography on silica gel (hexane eluent using Biotage). Fractions 11 through 21 are combined and concentrated on a rotary evaporator (1 g, 41%). The clear oil is transferred into a tared vial and then moved to a nitrogen atmosphere glove box.

Scheme 12

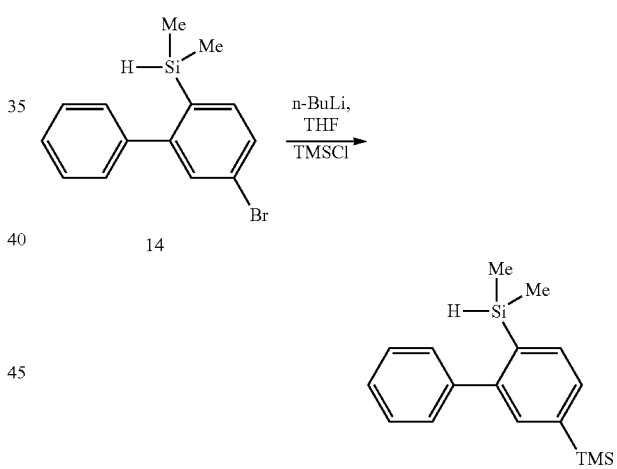

Compound 14 (3.86 g, 13.3 mmol) is dissolved in THF (100 mL). n-BuLi (10.0 mL, 1.6 M, 15.9 mmol) is added drop-wise and the reaction is warmed to 0° C. over 1 h. Trimethylsilylchloride (3.37 mL, 26.5 mmol) is then added and the reaction is stirred overnight. The reaction is poured into water and extracted with Et$_2$O. The organic layer is further washed with water and brine. The aqueous layers are extracted one additional time with Et$_2$O. The combined organics are dried over MgSO$_4$ and then concentrated under high vacuum. The resulting oil is purified by column chromatography using a 100 g SNAP column on the Biotage eluting with hexane. Upon concentration of these fractions the product is obtained as a colorless oil (2.87 g, 76%).

$^1$HNMR (400 MHz, CDCl$_3$) δ 7.62 (dd, J=7.3, 0.7 Hz, 1H), 7.52 (dd, J=7.3, 1.2 Hz, 1H), 7.46-7.31 (m, 7H), 4.32 (p, J=3.8 Hz, 1H), 0.28 (s, 9H), 0.06 (d, J=3.8 Hz, 6H).

$^{13}$C NMR (101 MHz, CDCl$_3$) δ 148.53, 144.16, 141.82, 136.63, 134.48, 134.14, 131.44, 129.43, 128.03, 127.23, −1.02, −2.89.

Scheme 13

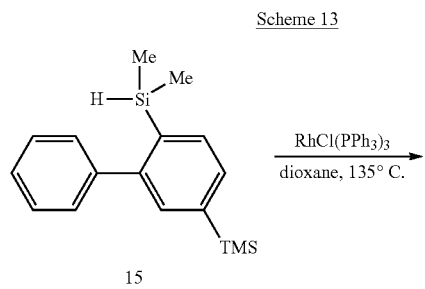

Compound 15 (2.87 g, 10.1 mmol) is added to a vial and diluted in dioxane (30 mL). RhCl(PPh$_3$)$_3$ (0.047 g, 0.051 mmol) is then added and the vial is transferred out of the box and placed in a pre-heated metal block at 135° C. After 3 h the reaction is analyzed by GC/MS showing 80% conversion. An additional equivalent of RhCl(PPh$_3$)$_3$ (0.047 g, 0.051 mmol) is added and heating is continued for 2 h upon which complete conversion is obtained. The solvent is removed and the crude residue is purified by column chromatography on silica gel eluting with hexane (1.96 g, 69%).

$^1$HNMR (400 MHz, CDCl$_3$) δ 7.99 (d, J=1.0 Hz, 1H), 7.89 (dt, J=7.8, 0.9 Hz, 1H), 7.65-7.60 (m, 2H), 7.47-7.40 (m, 2H), 7.30-7.25 (m, 1H), 0.42 (s, 6H), 0.32 (s, 9H).

$^{13}$C NMR (101 MHz, CDCl$_3$) δ: 149.01, 147.92, 143.59, 140.68, 140.01, 133.80, 133.41, 133.10, 131.17, 128.37, 126.41, 121.81, 0.00, −2.19.

Scheme 14

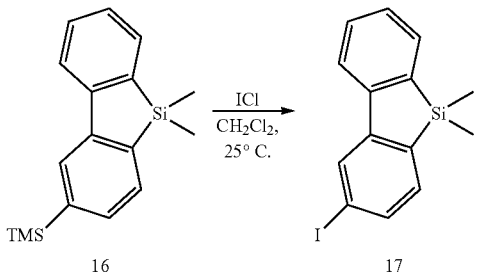

Compound 16 (1.96 g, 6.89 mmol) is dissolved in dichloromethane and cooled to −25° C., a solution of iodine monochloride (1.0 M in CH$_2$Cl$_2$, 6.9 mL) and the solution is stirred and warmed to room temperature over 1 h. An additional 0.69 mL of iodine monochloride solution is added and stirred for another 30 minutes when another 0.07 mL is added. The reaction is stirred for another 10 minutes and then is quenched with sodium thiosulfate (10% aqueous, 30 mL) and the reaction is stirred for 30 minutes. The organic layer is collected the aqueous layer is extracted with dichloromethane (2×20 mL). The combined organic fractions are rinsed further with water (2×40 mL), brine (40 mL), and dried with MgSO$_4$. The solution is filtered and concentrated. The resulting oil is then purified by column chromatography eluting with hexane. Upon concentration the desired product is isolated as a colorless oil (1.5 g, 65%).

$^1$H NMR (400 MHz, CDCl$_3$) δ: 8.16 (d, J=1.4 Hz, 1H), 7.76 (dt, J=7.8, 0.9 Hz, 1H), 7.66-7.57 (m, 2H), 7.43 (td, J=7.6, 1.4 Hz, 1H), 7.35 (d, J=7.5 Hz, 1H), 7.30 (td, J=7.3, 1.0 Hz, 1H), 0.41 (s, 6H).

$^{13}$C NMR (101 MHz, CDCl$_3$) δ: 149.92, 146.38, 138.97, 138.16, 136.05, 134.10, 132.79, 130.31, 130.13, 127.95, 121.03, 97.41, −3.40.

Scheme 15

Structure (iii)

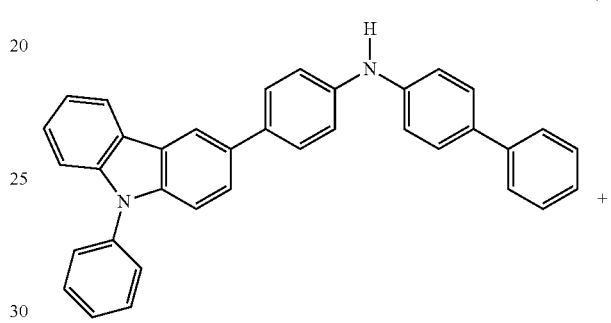

+

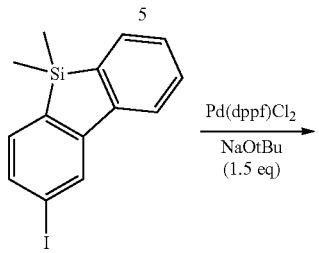

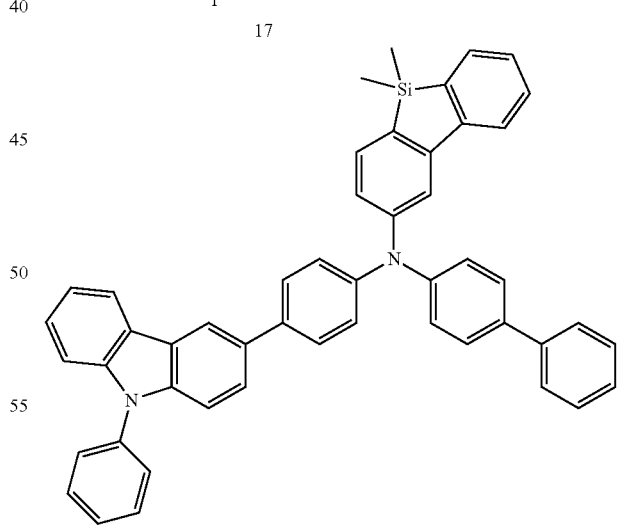

HTL-3

In a large flask is placed Compound 5 (1.0 g, 2.05 mmol) and 17 (0.69 g, 2.05 mmol), sodium t-butoxide (0.296 g, 3.08 mmol), and Pd(dppf).CHCl$_3$ (35 mg, 0.041 mmol). The reaction is diluted with toluene (10 mL) and the reaction is heated to 100° C. overnight. The reaction is then cooled and placed in a separatory funnel and the organic fraction is washed with water (2×100 mL). The water layer is again extracted with Et$_2$O (2×100 mL) and the combined organics are rinsed with brine (100 mL) and dried over Na$_2$SO$_4$. After filtration the volatiles are removed on a rotary evaporator. Residue is concentrated onto silica gel and chromatographed using a hexanes/dichloromethane gradient from 0 to 30% dichloromethane. The combined fractions are collected and dried to yield the product as a fluffy white solid. This reaction is repeated with the Compound 5 (1.45 g, 2.97 mmol), Compound 17 (1.0 g, 2.97 mmol), sodium t-butoxide (0.429 g, 4.46 mmol), and Pd(dppf).CHCl$_3$ (51 mg, 0.060 mmol) and toluene (20 mL). The purified material from the two reactions is combined to give 1.2 g (34% yield) of the desired product in 98% purity. Successive precipitation of this material from dichloromethane and acetonitrile yielded 0.996 g of the product in 99.8% purity.

$^1$H NMR (400 MHz, CDCl$_3$d) δ 8.36 (dd, J=1.8, 0.6 Hz, 1H), 8.19 (dt, J=7.8, 1.0 Hz, 1H), 7.70-7.57 (m, 10H), 7.54 (dd, J=8.3, 2.1 Hz, 3H), 7.53-7.43 (m, 3H), 7.47-7.38 (m, 3H), 7.39-7.20 (m, 10H), 7.08 (dd, J=7.8, 2.0 Hz, 1H), 0.45 (s, 6H).

$^{13}$C NMR (101 MHz, CDCl$_3$) δ 149.80, 149.37, 147.44, 146.99, 146.18, 141.36, 140.66, 140.22, 139.70, 137.71, 136.78, 135.45, 133.61, 132.95, 132.64, 132.33, 130.00, 129.91, 128.76, 128.08, 127.87, 127.49, 127.44, 127.07, 126.86, 126.70, 126.10, 125.18, 125.04, 124.38, 123.92, 123.50, 123.13, 120.97, 120.35, 120.05, 118.39, 116.40, 110.03, 109.92, −2.97.

4. OLED Device Fabrication and Testing

A. OLED Device

All organic materials are purified by sublimation before deposition. OLEDs are fabricated onto an ITO coated glass substrate that served as the anode, and topped with an aluminum cathode. All organic layers are thermally deposited by chemical vapor deposition, in a vacuum chamber with a base pressure of <10$^{-7}$ torr. The deposition rates of organic layers are maintained at 0.1~0.05 nm/s. The aluminum cathode is deposited at 0.5 nm/s. The active area of the OLED device is "3 mm×3 mm," as defined by the shadow mask for cathode deposition.

Each cell, containing HIL, HTL, EML host, EML dopant, ETL, or EIL, is placed inside a vacuum chamber, until it reaches 10$^{-6}$ torr. To evaporate each material, a controlled current is applied to the cell, containing the material, to raise the temperature of the cell. An adequate temperature is applied to keep the evaporation rate of the materials constant throughout the evaporation process.

For the HIL layer, N1,N1'-([1,1'-biphenyl]-4,4'-diyl)bis(N1-(naphthalen-1-yl)-N4,N4-diphenylbenzene-1,4-diamine) is evaporated at a constant 1 A/s rate, until the thickness of the layer reaches 600 Angstrom. Simultaneously, the HTL compounds are evaporated at a constant 1 A/s rate, until the thickness reaches 200 Angstrom. The N4,N4'-di(naphtalen-1-yl)-N4,N4'-diphenyl-[1,1'-biphenyl]-4,4'-diamine (NPB) is used as a reference material to compare with the present compositions. Other nonlimiting examples of HTL compounds include di(p-tolyl)aminophenyl]cyclohexane (TPAC), N,N-diphenyl-N,N-bis(3-methylphenyl)-1,1-biphenyl-4,4-diamine (TPD).

For the EML layer, 9,10-di(naphthalen-2-yl)anthracene (ADN, host) and (E)-4,4'-(ethene-1,2-diyl)bis-(N,N-diphenylaniline)(DPAVB, dopant) are co-evaporated, until the thickness reaches 350 Angstrom. The deposition rate for host material is 0.98 A/s, and the deposition for the dopant material is 0.02 A/s, resulting in a 2% doping of the host material. For the ETL layer, tris(8-hydroxyquinolinato)aluminum (Alq3) is evaporated at a constant 1 A/s rate, until the thickness reaches 300 Angstrom. Finally, "20 Angstrom" of a thin electron injection layer (Liq) is evaporated at a 0.2 A/s rate. See Table 2.

The current-voltage-brightness (J-V-L) characterizations for the OLED devices are performed with a source measurement unit (KEITHLY 238) and a luminescence meter (MINOLTA CS-100 A). Electroluminescence (EL) spectra of the OLED devices are collected by a calibrated CCD spectrograph.

TABLE 2

OLED Device Materials

| | Name | Commercial Name |
|---|---|---|
| Hole Injection Material | N1,N1'-([1,1'-biphenyl]-4,4'-diyl)bis(N1-(naphthalen-1-yl)-N4,N4-diphenylbenzene-1,4-diamine) | |
| Hole Transporting Material Or HTL-1 (Example 1) | N4,N4'-di(naphtalen-1-yl)-N4,N4'-diphenyl-[1,1'-biphenyl]-4,4'-diamine | NPB* |
| Fl Blue Host | 9,10-di(naphthalen-2-yl)anthracene | ADN |
| Fl Blue Dopant | (E)-4,4'-(ethane-1,2-diyl)bis(N,N-diphenylaniline) | DPAVB |
| Electron Transporting Material | tris(8-hydroxyquinolinato)aluminum | Alq3 |
| Electron Injection Material | lithium quinolate | Liq |

*comparative

B. OLED Device with Present Compositions

The present compositions are each further purified by sublimation, and incorporated into OLED devices for preliminary evaluation against the reference NPB.

OLED devices are fabricated, as discussed above, on coated glass substrates with multiple organic layers sandwiched between a transparent ITO anode and an aluminum cathode. OLED devices are produced as described above replacing the HTL layer (NBP, reference) with Example 1, HTL-1 (Structure (i)).

TABLE 3

OLED Device Data

|  | Voltage @1000 nit[1] [V] | Luminous Efficiency @1000 nit [Cd/A][2] | CIE[3] (X, Y) |
|---|---|---|---|
| NPB* | 6.6 | 4.0 | 148, 150 |
| Example 1 HTL-1 with Structure (i) | 6.4 | 4.8 | 148, 152 |

*comparative
[1] Nit = candela per square meter (Cd/m$^2$)
[2] Cd/A = candelas per ampere (Amp)
[3] CIE = The International Commission on Illumination Table 3 shows the OLED device testing results of Example 1 compared to reference compound, NPB in the HTL.

As seen in Table 3, the device using Example 1, HTL-1 (Structure (i)), exhibits better (higher) efficiency when compared to the device containing the reference compound, NPB, for the HTL layer.

It is specifically intended that the present disclosure not be limited to the embodiments and illustrations contained herein, but include modified forms of those embodiments including portions of the embodiments and combinations of elements of different embodiments as come within the scope of the following claims.

The invention claimed is:

1. A composition comprising a Compound 1:

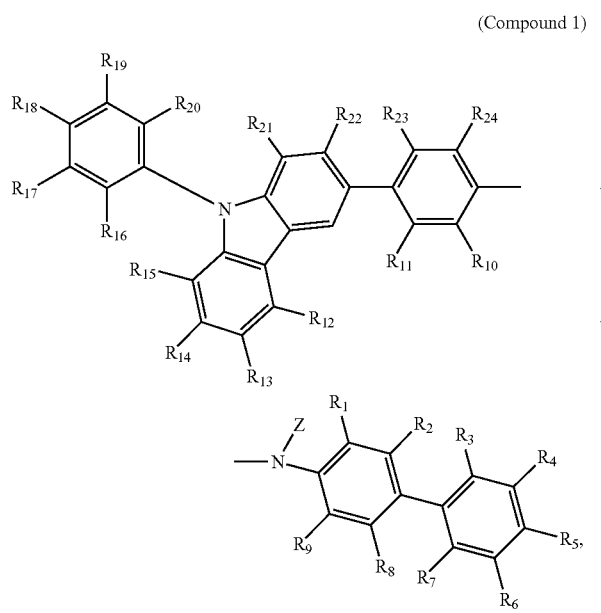

(Compound 1)

wherein $R_1$ through $R_{24}$ are the same or different and each of $R_1$ through $R_{24}$ is independently selected from the group consisting of hydrogen, unsubstituted hydrocarbyl, and substituted hydrocarbyl;

wherein two or more of adjacent $R_1$ to $R_{24}$ may optionally form one or more ring structures; and Z is selected from the group consisting of Group Z-2, Group Z-4, Group Z-5, Group Z-6, and Group Z-7 shown below

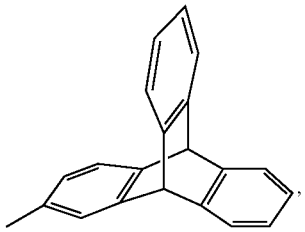
Group Z-2

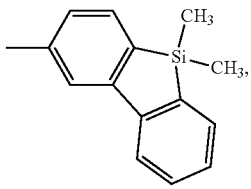
Group Z-3

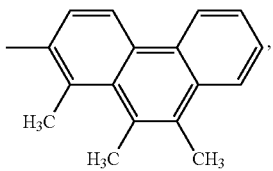
Group Z-4

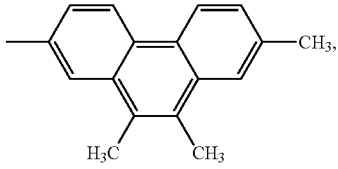
Group Z-5

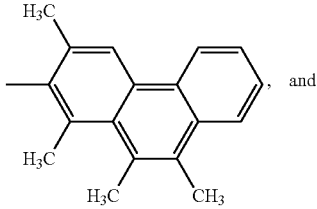
Group Z-6, and

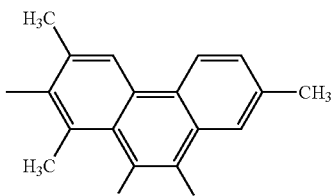
Group Z-7 wherein, for Compound 1, one or more hydrogen atoms may optionally be substituted with deuterium.

2. The composition of claim 1, wherein $R_1$ through $R_{24}$ each is hydrogen.

3. The composition of claim 1, wherein Compound 1 has a HOMO level from −4.50 eV to −4.90 eV.

4. The composition of claim 1, wherein Compound 1 has a SUMO level from 0.00 eV to −1.10 eV.

5. The composition of claim 1, wherein Compound 1 has a triplet energy level from 2.50 eV to 3.30 eV.

6. The composition of claim 1, wherein Compound 1 has a molecular weight from 500 g/mole to 1000 g/mole.

7. The composition of claim 1, wherein Compound 1 has a glass transition temperature, Tg, from 110° C. to 180° C., as determined by DSC.

8. A composition comprising a Compound 1:

(Compound 1)

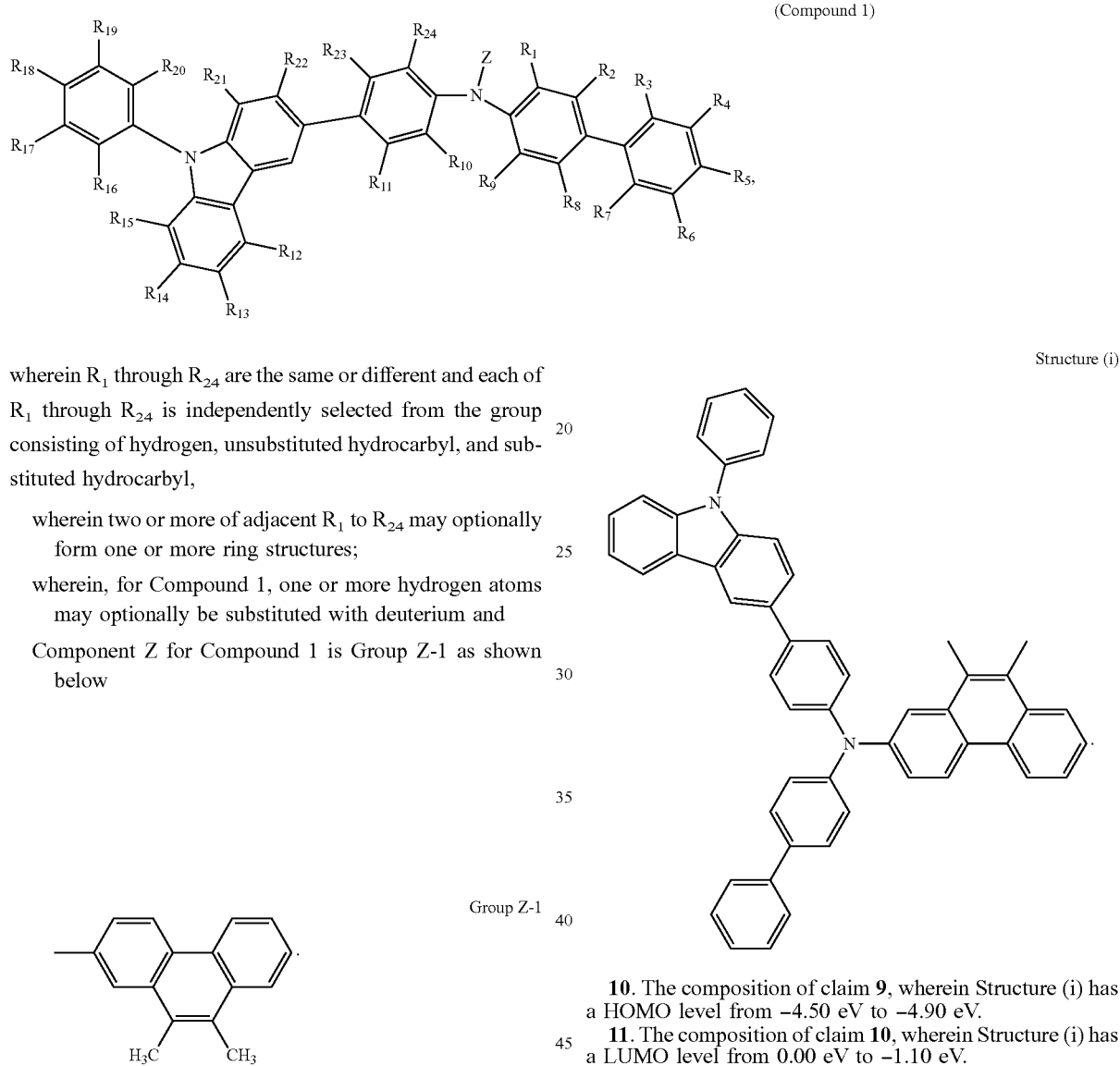

wherein $R_1$ through $R_{24}$ are the same or different and each of $R_1$ through $R_{24}$ is independently selected from the group consisting of hydrogen, unsubstituted hydrocarbyl, and substituted hydrocarbyl, wherein two or more of adjacent $R_1$ to $R_{24}$ may optionally form one or more ring structures;

wherein, for Compound 1, one or more hydrogen atoms may optionally be substituted with deuterium and Component Z for Compound 1 is Group Z-1 as shown below Group Z-1

9. The composition of claim 8, wherein Compound 1 has the Structure (i) as shown below Structure (i)

10. The composition of claim 9, wherein Structure (i) has a HOMO level from −4.50 eV to −4.90 eV.

11. The composition of claim 10, wherein Structure (i) has a LUMO level from 0.00 eV to −1.10 eV.

12. The composition of claim 11, wherein Structure (i) has a triplet energy level from 2.50 to 3.30 eV.

13. A film formed from the composition of claim 1.

14. An electronic device comprising at least one component formed from the composition of claim 1.

15. A composition comprising a Compound 1:

(Compound 1)

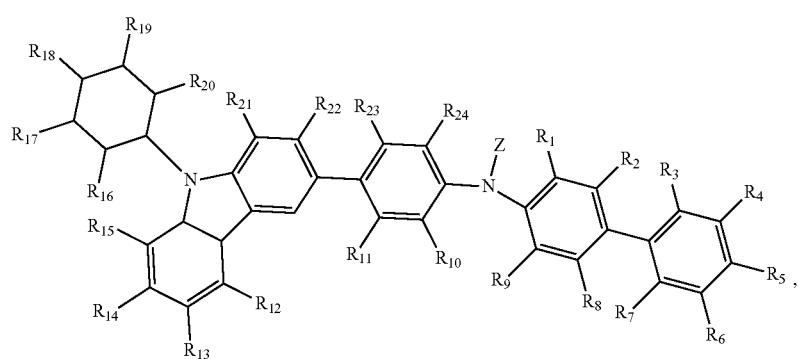

wherein R₁ through R₂₄ are the same or different and each of R₁ through R₂₄ is independently selected from the group consisting of hydrogen, unsubstituted hydrocarbyl, and substituted hydrocarbyl;

wherein two or more of adjacent R₁ to R₂₄ may optionally form one or more ring structures; and Z is selected from the group consisting of Group Z-2 and Group Z-4, shown below Group Z-2

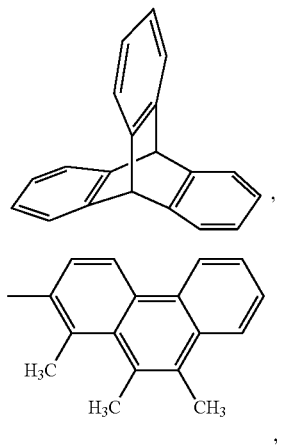

Group Z-4 wherein, for Compound 1, one or more hydrogen atoms may optionally be substituted with deuterium.

16. The composition of claim 15 wherein R₁ through R₂₄ are the same or different and each of R₁ through R₂₄ is independently selected from the group consisting of hydrogen, unsubstituted hydrocarbyl, substituted hydrocarbyl; and Component Z for Compound 1 is Group Z-2 as shown below Group Z-2

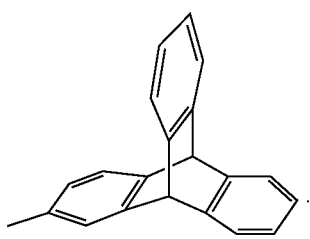

17. The composition of claim 16, wherein Compound 1 has the Structure (ii) as shown below Structure (iii)

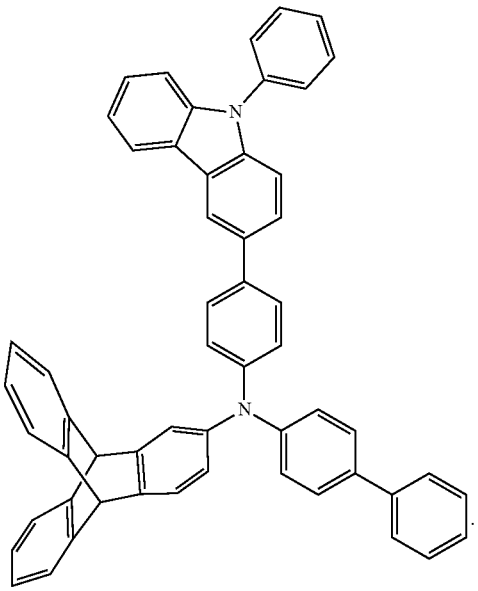

18. The composition of claim 15 wherein R₁ through R₂₄ are the same or different and each of R₁ through R₂₄ is independently selected from the group consisting of hydrogen, unsubstituted hydrocarbyl, substituted hydrocarbyl; and Component Z for Compound 1 is Group Z-4 as shown below Group Z-4

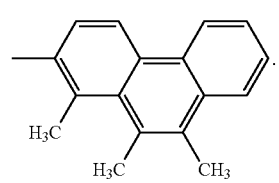

* * * * *